United States Patent [19]
Chou et al.

[11] Patent Number: 6,056,957
[45] Date of Patent: May 2, 2000

[54] HUMANIZED MONOCLONAL ANTIBODIES AGAINST HUMAN INTERLEUKIN-5

[75] Inventors: Chuan-Chu Chou, Westfield; Nicholas J. Murgolo, Millington, both of N.J.; John S. Abrams, Belmont, Calif.; Chung-Her Jenh, Edison; Mary E. Petro, Green Pond, both of N.J.; Jon E. Silver, San Jose, Calif.; Stephen Tindall, Madison, N.J.; William T. Windsor, East Brunswick, N.J.; Paul J. Zavodny, Mountainside, N.J.

[73] Assignee: Schering Corporation, Kenilworth, N.J.

[21] Appl. No.: 08/284,516

[22] Filed: Aug. 4, 1994

Related U.S. Application Data

[63] Continuation-in-part of application No. 07/832,842, filed as application No. PCT/US93/00759, Feb. 4, 1993, abandoned.

[51] Int. Cl.[7] .................. A61K 39/395; C07K 16/24; C12N 15/13; C12N 5/12
[52] U.S. Cl. ................ 424/145.1; 424/130.1; 424/133.1; 424/141.1; 424/158.1; 435/69.1; 435/69.6; 435/70.21; 435/326; 435/335; 435/346; 530/387.1; 530/387.3; 530/388.1; 530/388.23; 536/23.1; 536/23.4; 536/23.53; 536/23.5
[58] Field of Search ............... 530/387.1, 388.23; 536/23.53, 23.1, 23.5; 435/69.1, 252.3, 326; 424/130.1, 145.1

[56] References Cited

U.S. PATENT DOCUMENTS

| | | |
|---|---|---|
| 5,091,513 | 2/1992 | Huston et al. . |
| 5,096,704 | 3/1992 | Coffman et al. . |
| 5,530,101 | 6/1996 | Queen et al. . |

FOREIGN PATENT DOCUMENTS

| | | |
|---|---|---|
| 0 239 400 | 9/1987 | European Pat. Off. . |
| 368684 | 5/1990 | European Pat. Off. . |
| WO 89/01783 | 3/1989 | WIPO . |
| WO 91/17179 | 11/1991 | WIPO . |
| WO 93/16184 | 8/1993 | WIPO . |

OTHER PUBLICATIONS

Blood 77: xxxiii–xxxv (1991) Information For Contributor.
Denburg, J. A. et al. Blood 77: 1462–1468, Apr. 1991.
Queen, C. et al. Proc. Natl. Acad. Sci. USA 86: 10029–10033, Dec. 1989.
Riechmann, L. et al. Nature 332: 323–327, Mar. 1988.
Brennan et al., Science 229:81 (1985).
Denburg et al., Blood 77(7):1462 (1991).
Geysen et al., J. Immunol. Meth. 102:259 (1987).
Jameson et al., Nature 341:465 (1989).
Kabat et al., *Sequences of Proteins of Immunological Interest*, 4th Edition, 1987, U.S. Dept. of Health & Human Services, National Institutes of Health.
Köhler and Milstein, Eur. J. Immunol. 6:511 (1976).
Larrick et al., Bio/Technology 7:934 (1989).
Lewis et al., Gene 101(2):297 (1991).
Liu et al., Proc. Natl. Acad. Sci. USA 84:3439 (1987).
Milstein, *Immunology Recognition and Response*, 1991, W.E. Paul, Ed. W.H. Freedman & Company, New York, pp. 124–134.
Miyajima et al., TIBS 17:378 (1992).
Queen et al., Proc. Natl. Acad. Sci. USA 86:10029 (1989).
Regenmortel, *Immunogenicity of Protein Antigens: Repertoire and Regulation*, 1987, E. Sercarz and J. Borzofsky, Eds., CRC Press, Inc., Boca Raton, Florida, pp. 21–28.
Riechmann et al., Nature 332:323 (1988).
Saiki et al., Science 239:487 (1988).
Saragovi et al., Science 253:792 (1991).
Schmitter et al., Mol. Immunol. 27:1029 (1990).
Shulman et al., Nature 276:269 (1978).
Tavernier et al., DNA 8(7):491 (1989).
Zurawksi et al., EMBO J. 8:2583 (1989).

*Primary Examiner*—Christina Y. Chan
*Assistant Examiner*—Phillip Gambel
*Attorney, Agent, or Firm*—Kenneth M. Goldman; Cynthia L. Foulke

[57] ABSTRACT

A monoclonal antibody is provided which specifically binds to human interleukin-5. Also provided are a hybridoma which produces the monoclonal antibody; complementary DNAs which encode the heavy and light chain variable regions of the monoclonal antibody and CDRs therefrom; humanized monoclonal antibodies; and pharmaceutical compositions comprising the monoclonal antibody or anti-idiotypic antibodies directed against it, humanized monoclonal antibodies, binding fragments, binding compositions or single-chain binding proteins derived from the antibody and a physiologically acceptable carrier.

30 Claims, 4 Drawing Sheets

SEQUENCE LISTING (1) GENERAL INFORMATION:

(iii) NUMBER OF SEQUENCES:   66

(2) INFORMATION FOR SEQ ID NO: 1:

(i) SEQUENCE CHARACTERISTICS:
        (A) LENGTH:    333 base pairs
        (B) TYPE:    nucleic acid
        (C) STRANDEDNESS:    double
        (D) TOPOLOGY:    linear (xi) SEQUENCE DESCRIPTION: SEQ ID NO: 1:

```
GAA TCT GGA GGA GGC TTG GTA CAG CCA TCA CAG ACC CTG TCT CTC ACC      48
Glu Ser Gly Gly Gly Leu Val Gln Pro Ser Gln Thr Leu Ser Leu Thr
              5                  10                  15

TGC ACT GTC TCT GGG TTA TCA TTA ACC AGC AAT AGT GTG AAC TGG ATT      96
Cys Thr Val Ser Gly Leu Ser Leu Thr Ser Asn Ser Val Asn Trp Ile
             20                  25                  30

CGG CAG CCT CCA GGA AAG GGT CTG GAG TGG ATG GGA CTA ATA TGG AGT     144
Arg Gln Pro Pro Gly Lys Gly Leu Glu Trp Met Gly Leu Ile Trp Ser
         35                  40                  45

AAT GGA GAC ACA GAT TAT AAT TCA GCT ATC AAA TCC CGA CTG AGC ATC     192
Asn Gly Asp Thr Asp Tyr Asn Ser Ala Ile Lys Ser Arg Leu Ser Ile
     50                  55                  60

AGT AGG GAC ACC TCG AAG AGC CAG GTT TTC TTA AAG ATG AAC AGT CTG     240
Ser Arg Asp Thr Ser Lys Ser Gln Val Phe Leu Lys Met Asn Ser Leu
 65                  70                  75                  80

CAA AGT GAA GAC ACA GCC ATG TAC TTC TGT GCC AGA GAG TAC TAC GGC     288
Gln Ser Glu Asp Thr Ala Met Tyr Phe Cys Ala Arg Glu Tyr Tyr Gly
                 85                  90                  95

TAC TTT GAT TAC TGG GGC CAA GGA GTC ATG GTC ACA GTC TCC TCA         333
Tyr Phe Asp Tyr Trp Gly Gln Gly Val Met Val Thr Val Ser Ser
            100                 105                 110
```

(2) INFORMATION FOR SEQ ID NO: 2:

(i) SEQUENCE CHARACTERISTICS:
        (A) LENGTH:   384 base pairs
        (B) TYPE:   nucleic acid
        (C) STRANDEDNESS:   double
        (D) TOPOLOGY:   linear (xi) SEQUENCE DESCRIPTION: SEQ ID NO: 2:

```
ATG GCT GTG CCC ACT CAG CTC CTG GGG TTG TTG TTG CTG TGG ATT ACA        48
Met Ala Val Pro Thr Gln Leu Leu Gly Leu Leu Leu Leu Trp Ile Thr
              5                  10                  15

GAT GCC ATA TGT GAC ATC CAG ATG ACA CAG TCT CCA GCT TCC CTG TCT        96
Asp Ala Ile Cys Asp Ile Gln Met Thr Gln Ser Pro Ala Ser Leu Ser
         20                  25                  30

GCA TCT CTG GGA GAA ACT ATC TCC ATC GAA TGT CTA GCA AGT GAG GGC       144
Ala Ser Leu Gly Glu Thr Ile Ser Ile Glu Cys Leu Ala Ser Glu Gly
     35                  40                  45

ATT TCC AGT TAT TTA GCG TGG TAT CAG CAG AAG CCA GGG AAA TCT CCT       192
Ile Ser Ser Tyr Leu Ala Trp Tyr Gln Gln Lys Pro Gly Lys Ser Pro
 50                  55                  60

CAG CTC CTG ATC TAT GGT GCA AAT AGC TTG CAA ACT GGG GTC CCA TCA       240
Gln Leu Leu Ile Tyr Gly Ala Asn Ser Leu Gln Thr Gly Val Pro Ser
 65                  70                  75                  80

CGG TTC AGT GGC AGT GGA TCT GCC ACA CAA TAT TCT CTC AAG ATC AGC       288
Arg Phe Ser Gly Ser Gly Ser Ala Thr Gln Tyr Ser Leu Lys Ile Ser
                 85                  90                  95

AGC ATG CAA CCT GAA GAT GAA GGG GAT TAT TTC TGT CAA CAG AGT TAC       336
Ser Met Gln Pro Glu Asp Glu Gly Asp Tyr Phe Cys Gln Gln Ser Tyr
            100                 105                 110

AAG TTT CCG AAC ACG TTT GGA GCT GGG ACC AAG CTG GAA CTG AAA CGG       384
Lys Phe Pro Asn Thr Phe Gly Ala Gly Thr Lys Leu Glu Leu Lys Arg
        115                 120                 125
```

(2) INFORMATION FOR SEQ ID NO: 3:

(i) SEQUENCE CHARACTERISTICS:
        (A) LENGTH:   39 base pairs
        (B) TYPE:   nucleic acid
        (C) STRANDEDNESS:   single
        (D) TOPOLOGY:   linear (xi) SEQUENCE DESCRIPTION: SEQ ID NO: 3:

AGTCTAGAAG CTTGAATCTG GAGGAGGCTT GGTACAGCC        39

(2) INFORMATION FOR SEQ ID NO: 4:

(i) SEQUENCE CHARACTERISTICS:
        (A) LENGTH:   58 base pairs
        (B) TYPE:   nucleic acid
        (C) STRANDEDNESS:   single
        (D) TOPOLOGY:   linear (xi) SEQUENCE DESCRIPTION: SEQ ID NO: 4:

CAGCCCGGGA ATTCGTCGAC TCACTGCCAT GTTTCTTTCT TTACATTGAG CTTGCTGT        58

(2) INFORMATION FOR SEQ ID NO: 5:

(i) SEQUENCE CHARACTERISTICS:
        (A) LENGTH:   36 base pairs
        (B) TYPE:   nucleic acid
        (C) STRANDEDNESS:   single
        (D) TOPOLOGY:   linear (xi) SEQUENCE DESCRIPTION: SEQ ID NO: 5:

```
GCAAGCTTGG ATCCAGACAG GACACAGGCC AGACAT                                    36

(2) INFORMATION FOR SEQ ID NO: 6:

(i) SEQUENCE CHARACTERISTICS:
          (A) LENGTH:   38 base pairs
          (B) TYPE:     nucleic acid
          (C) STRANDEDNESS:   single
          (D) TOPOLOGY:  linear (xi) SEQUENCE DESCRIPTION: SEQ ID NO: 6:

CACGAATTCT GCAGTGGCAC CTCAGGACCT TTGGGTCT                                  38

(2) INFORMATION FOR SEQ ID NO: 7:

(i) SEQUENCE CHARACTERISTICS:
          (A) LENGTH:   114 base pairs
          (B) TYPE:     nucleic acid
          (C) STRANDEDNESS:   single
          (D) TOPOLOGY:  linear (xi) SEQUENCE DESCRIPTION: SEQ ID NO: 7:

AGGCAGTCGA CGCCGCCACC ATGAAGTTGT GGCTGAACTG GATTTTCCTT TTAACACTTT          60

TAAATGGTAT CCAGTGTGAG GTGAAACTGT TGGAATCTGG AGGAGGCTTG GTAC               114

(2) INFORMATION FOR SEQ ID NO: 8:

(i) SEQUENCE CHARACTERISTICS:
          (A) LENGTH:   131 base pairs
          (B) TYPE:     nucleic acid
          (C) STRANDEDNESS:   single
          (D) TOPOLOGY:  linear (xi) SEQUENCE DESCRIPTION: SEQ ID NO: 8:

ACTGAATTCT ATTTACCAGG AGAGTGGGAG AGACTCTTCT CAGTATGGTG GTTGTGCAGG          60

CCCTCATGCA GCACAGAACA CGTGAAAGTG TTTCCCTGCT GCCATGTTTC TTTCTTTACA        120

TTGAGCTTGC T                                                             131

(2) INFORMATION FOR SEQ ID NO: 9:

(i) SEQUENCE CHARACTERISTICS:
          (A) LENGTH:   66 base pairs
          (B) TYPE:     nucleic acid
          (C) STRANDEDNESS:   single
          (D) TOPOLOGY:  linear (xi) SEQUENCE DESCRIPTION: SEQ ID NO: 9:

AGCTGTCGAC GCCGCCACCA TGCGTTGTGC CACTCAGCTC CTGGGGTTGT TGTTGCTGTG          60

GATTAC                                                                    66

(2) INFORMATION FOR SEQ ID NO: 10:

(i) SEQUENCE CHARACTERISTICS:
          (A) LENGTH:   48 base pairs
          (B) TYPE:     nucleic acid
          (C) STRANDEDNESS:   single
          (D) TOPOLOGY:  linear (xi) SEQUENCE DESCRIPTION: SEQ ID NO: 10:

AGCTCTAGAA TTCTGCAGTC AACACTCATT CCTGTTGAAG CTCTTGAC                       48

(2) INFORMATION FOR SEQ ID NO: 11:

(i) SEQUENCE CHARACTERISTICS:
```

(A) LENGTH: 102 base pairs
(B) TYPE: nucleic acid
(C) STRANDEDNESS: single
(D) TOPOLOGY: linear (xi) SEQUENCE DESCRIPTION: SEQ ID NO: 11:

```
GCTGAATTCG CCGCCACCAT GGGCTGGAGC TGTATCATCC TCTTCTTAGT AGCAACAGCT    60

ACAGGTGTCC ACTCCCAGGT CAAACTGGTA CAAGCTGGAG GT                      102
```

(2) INFORMATION FOR SEQ ID NO: 12:

(i) SEQUENCE CHARACTERISTICS:
        (A) LENGTH: 102 base pairs
        (B) TYPE: nucleic acid
        (C) STRANDEDNESS: single
        (D) TOPOLOGY: linear (xi) SEQUENCE DESCRIPTION: SEQ ID NO: 12:

```
GCGTACTAGT TAATGATAAC CAGAGACGA TGCAACTCAG TCGCAGAGAT CTTCCTGGCT     60

GTACGACGCC ACCTCCAGCT TGTACCAGTT TGACCTGGGA GT                      102
```

(2) INFORMATION FOR SEQ ID NO: 13:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 13:

```
GTCAGACTAG TAATAGTGTG AACTGGATAC GGCAAGCACC TGGCAAGGGT CTGGAGTGGG    60

TTGCACTAAT ATGGAGTAAT GGAGAC                                         86
```

(2) INFORMATION FOR SEQ ID NO: 14:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (xi) SEQUENCE DESCRIPTION: SEQ ID NO: 14:

```
GTACTCTAGA GATTGTGAAT CGAGATTTGA TAGCTGAATT ATAATCTGTG TCTCCATTAC    60

TCCATATTAG TGC                                                       73
```

(2) INFORMATION FOR SEQ ID NO: 15:

(i) SEQUENCE CHARACTERISTICS:
        (A) LENGTH: 104 base pairs
        (B) TYPE: nucleic acid
        (C) STRANDEDNESS: single
        (D) TOPOLOGY: linear (xi) SEQUENCE DESCRIPTION: SEQ ID NO: 15:

```
GCAGAATTCT AGAGACAATT CGAAGAGCAC CCTATACATG CAGATGAACA GTCTGAGAAC    60

TGAAGATACT GCAGTCTACT TCTGTGCTCG TGAGTACTAT GGAT                    104
```

(2) INFORMATION FOR SEQ ID NO:16:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (xi) SEQUENCE DESCRIPTION: SEQ ID NO: 16:

CTCGTGAGCT CGGGCCCTTG GTCGACGCTG AGGAGACTGT GACTAGGACA CCTTGACCCC     60

AATAGTCGAA ATATCCATAG TACTCACGAG CACAGAAGT                            99

(2) INFORMATION FOR SEQ ID NO: 17:

(i) SEQUENCE CHARACTERISTICS:
      (A) LENGTH:   94 base pairs
      (B) TYPE:   nucleic acid
      (C) STRANDEDNESS:   single
      (D) TOPOLOGY:   linear (xi) SEQUENCE DESCRIPTION: SEQ ID NO: 17:

AGAGCTGCAG CCGCCACCAT GGGATGGAGC TGTATCATCC TCTTCTTGGT AGCAACAGCT     60

ACAGGTGTCC ACTCCGACAT CCAGATGACA CAGT                                94

(2) INFORMATION FOR SEQ ID NO: 18:

(i) SEQUENCE CHARACTERISTICS:
      (A) LENGTH:   83 base pairs
      (B) TYPE:   nucleic acid
      (C) STRANDEDNESS:   single
      (D) TOPOLOGY:   linear (xi) SEQUENCE DESCRIPTION: SEQ ID NO: 18:

AGCATCTAGA GGTGACCCTA TCTCCGACAG ATACAGACAG CGAACTTGGA GACTGTGTCA     60

TCTGGATGTC GGAGTGGACA CCT                                            83

(2) INFORMATION FOR SEQ ID NO: 19:

(i) SEQUENCE CHARACTERISTICS:
      (A) LENGTH:   101 base pairs
      (B) TYPE:   nucleic acid
      (C) STRANDEDNESS:   single
      (D) TOPOLOGY:   linear (xi) SEQUENCE DESCRIPTION: SEQ ID NO: 19:

AGATCTGCAG GTCACCATCA CATGTCTAGC AAGTGAGGGC ATCTCCAGTT ACTTAGCGTG     60

GTACCAGCAG AAGCCCGGGC TAGCTCCTAA GCTCCTGATC T                        101

(2) INFORMATION FOR SEQ ID NO: 20:

(i) SEQUENCE CHARACTERISTICS:
      (A) LENGTH:   84 base pairs
      (B) TYPE:   nucleic acid
      (C) STRANDEDNESS:   single
      (D) TOPOLOGY:   linear (xi) SEQUENCE DESCRIPTION: SEQ ID NO: 20:

ATGGCGGATC CTGAGCCACT GAATCTTGAT GGTACTCCAG TCTGCAAGCT ATTCGCACCA     60

TAGATCAGGA GCTTAGGAGC TAGC                                           84

(2) INFORMATION FOR SEQ ID NO: 21:

(i) SEQUENCE CHARACTERISTICS:
      (A) LENGTH:   81 base pairs
      (B) TYPE:   nucleic acid
      (C) STRANDEDNESS:   single
      (D) TOPOLOGY:   linear (xi) SEQUENCE DESCRIPTION: SEQ ID NO: 21:

CTCAGGATCC GCTACAGACT TCACGCTCAC GATCTCCAGC CTACAGCCTG AAGATATCGC     60

```
GACGTATTAC TGTCAACAGT C                                                    81

(2) INFORMATION FOR SEQ ID NO: 22:

(i) SEQUENCE CHARACTERISTICS:
        (A) LENGTH:   76 base pairs
        (B) TYPE:   nucleic acid
        (C) STRANDEDNESS:   single
        (D) TOPOLOGY:   linear (xi) SEQUENCE DESCRIPTION: SEQ ID NO: 22:

GCATGCCGTC GACCTTGGTG CCTTGACCGA ATGTGTTCGG GAACTTATAC GACTGTTGAC          60

AGTAATACGT CGCGAT                                                          76

(2) INFORMATION FOR SEQ ID NO: 23:

(i) SEQUENCE CHARACTERISTICS:
        (A) LENGTH:   70 base pairs
        (B) TYPE:   nucleic acid
        (C) STRANDEDNESS:   single
        (D) TOPOLOGY:   linear (xi) SEQUENCE DESCRIPTION: SEQ ID NO: 23:

GCATCGCGTC GACCAAAGGT CCATCTGTGT TTCCGCTGGC GCCATGCTCC AGGAGCACCT          60

CCGAGAGCAC                                                                 70

(2) INFORMATION FOR SEQ ID NO: 24:

(i) SEQUENCE CHARACTERISTICS:
        (A) LENGTH:   79 base pairs
        (B) TYPE:   nucleic acid
        (C) STRANDEDNESS:   single
        (D) TOPOLOGY:   linear (xi) SEQUENCE DESCRIPTION: SEQ ID NO: 24:

GACAGAATTC AGGTGCTGGA CACGACGGAC ATGGAGGACC ATACTTCGAC TCAACTCTCT          60

TGTCCACCTT GGTGTTGCT                                                       79

(2) INFORMATION FOR SEQ ID NO: 25:

(i) SEQUENCE CHARACTERISTICS:
        (A) LENGTH:   68 base pairs
        (B) TYPE:   nucleic acid
        (C) STRANDEDNESS:   single
        (D) TOPOLOGY:   linear (xi) SEQUENCE DESCRIPTION: SEQ ID NO: 25:

ACTGGAATTC CTAGGTGGAC CATCAGTCTT CCTGTTTCCG CCTAAGCCCA AGGACACTCT          60

CATGATCT                                                                   68

(2) INFORMATION FOR SEQ ID NO: 26:

(i) SEQUENCE CHARACTERISTICS:
        (A) LENGTH:   51 base pairs
        (B) TYPE:   nucleic acid
        (C) STRANDEDNESS:   single
        (D) TOPOLOGY:   linear (xi) SEQUENCE DESCRIPTION: SEQ ID NO: 26:

CAGGCTGTCG ACTCGAGGCT GACCTTTGGC TTTGGAGATG GTTTTCTCGA T                   51

(2) INFORMATION FOR SEQ ID NO: 27:
```

```
    (i) SEQUENCE CHARACTERISTICS:
         (A) LENGTH:  38 base pairs
         (B) TYPE:  nucleic acid
         (C) STRANDEDNESS:  single
         (D) TOPOLOGY:  linear (xi) SEQUENCE DESCRIPTION: SEQ ID NO: 27:

GTAAGCGTCG ACTCGAGAGC CACAGGTGTA CACCCTGC                              38

(2) INFORMATION FOR SEQ ID NO: 28:

(i) SEQUENCE CHARACTERISTICS:
         (A) LENGTH:  40 base pairs
         (B) TYPE:  nucleic acid
         (C) STRANDEDNESS:  single
         (D) TOPOLOGY:  linear (xi) SEQUENCE DESCRIPTION: SEQ ID NO: 28:

CGCTAGCGGC CGCTCATTTA CCCAGAGACA GGGAGAGGCT                            40

(2) INFORMATION FOR SEQ ID NO: 29:

(i) SEQUENCE CHARACTERISTICS:
         (A) LENGTH:  196 base pairs
         (B) TYPE:  nucleic acid
         (C) STRANDEDNESS:  single
         (D) TOPOLOGY:  linear (xi) SEQUENCE DESCRIPTION: SEQ ID NO: 29:

AGTGCGCTGC AGCCGCCACC ATGGGATGGA GCTGTATCAT CCTCTTCTTG GTAGCAACAG      60

CTACAGGTGT CCACTCCGAC ATCCAGATGA CACAGTCTCC AAGTTCCCTG TCTGCATCTG     120

TCGGAGATCG GGTCACAATC GAATGTCTAG CAAGTGAGGG CATTTCCAGT TATTTAGCGT     180

GGTATCAGCA GAAGCC                                                    196

(2) INFORMATION FOR SEQ ID NO: 30:

(i) SEQUENCE CHARACTERISTICS:
         (A) LENGTH:  213 base pairs
         (B) TYPE:  nucleic acid
         (C) STRANDEDNESS:  single
         (D) TOPOLOGY:  linear (xi) SEQUENCE DESCRIPTION: SEQ ID NO: 30:

ACCTTGGTAC CTTGTCCAAA CGTGTTCGGA AACTTGTAAC TCTGTTGACA GTAATAATCT      60

CCTTCATCTT CAGGTTGCAG GCTGGAGATC TTAAACGTGA AATCTGTGCC GGATCCACTG     120

CCACTGAACC GTGATGGGAC CCCAGTTTGC AAGCTATTTG CACCATAGAT CAGGAGTTTA     180

GGAGCTTTCC CTGGCTTCTG CTGATACCAC GCT                                 213

(2) INFORMATION FOR SEQ ID NO: 31:

(i) SEQUENCE CHARACTERISTICS:
         (A) LENGTH:  190 base pairs
         (B) TYPE:  nucleic acid
         (C) STRANDEDNESS:  single
         (D) TOPOLOGY:  linear (xi) SEQUENCE DESCRIPTION: SEQ ID NO: 31:

GAACACGTTT GGACAAGGTA CCAAGGTCGA CATCAAACGG ACTGTGGCTG CACCATCTGT      60

CTTCATCTTC CCGCCATCTG ATGAGCAGTT GAAATCTGGA ACTGCCTCTG TTGTGTGCCT     120

GCTGAATAAC TTCTATCCCA GAGAGGCCAA AGTACAGTGG AAGGTGGATA ACGCCCTCCA     180

ATCGGGTAAC                                                           190
```

(2) INFORMATION FOR SEQ ID NO: 32:

(i) SEQUENCE CHARACTERISTICS:
        (A) LENGTH: 207 base pairs
        (B) TYPE: nucleic acid
        (C) STRANDEDNESS: single
        (D) TOPOLOGY: linear (xi) SEQUENCE DESCRIPTION: SEQ ID NO: 32:

```
GTCAGAATTC TAACACTCTC CCCTGTTGAA GCTCTTTGTG ACGGGCGAGC TCAGGCCCTG      60

ATGGGTGACT TCGCAGGCGT AGACTTTGTG TTTCTCGTAG TCTGCTTTGC TCAGCGTCAG     120

GGTGCTGCTG AGGCTGTAGG TGCTGTCCTT GCTGTCCTGC TCTGTGACAC TCTCCTGGGA     180

GTTACCCGAT GGAGGGCGT TATCCAC                                          207
```

(2) INFORMATION FOR SEQ ID NO: 33:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO: 33:

```
GCATGCGTCG ACGTCAAACG GACTGTGGCT GC                                    32
```

(2) INFORMATION FOR SEQ ID NO: 34:

(i) SEQUENCE CHARACTERISTICS:
        (A) LENGTH: 111 base pairs
        (B) TYPE: nucleic acid
        (C) STRANDEDNESS: single
        (D) TOPOLOGY: linear (xi) SEQUENCE DESCRIPTION: SEQ ID NO: 34:

```
GATCAAGCTT GAATTCTAAC ACTCTCCTCT GTTGAAGCTC TTCGTGACTG GCGAGCTCAG      60

GCCTTGATGA GTGACTTCGC AGGCGTAGAC TTTGTGTTTC TCGTAGTCTG C              111
```

(2) INFORMATION FOR SEQ ID NO: 35:

(i) SEQUENCE CHARACTERISTICS:
        (A) LENGTH: 117 base pairs
        (B) TYPE: nucleic acid
        (C) STRANDEDNESS: single
        (D) TOPOLOGY: linear (xi) SEQUENCE DESCRIPTION: SEQ ID NO: 35:

```
GAGTCAGTCC AAGCTTGAAT TCTAACACTC TCCTCTGTTG AAGCTCTTCG TGACTGGCGA      60

GCTCAGGCCT TGATGAGTGA CTTCGCAGGC GTAGACTTTG TGTTTCTCGT AGTCTGC        117
```

(2) INFORMATION FOR SEQ ID NO: 36:

(i) SEQUENCE CHARACTERISTICS:
        (A) LENGTH: 135 amino acids
        (B) TYPE: amino acid
        (D) TOPOLOGY: linear (ii) MOLECULE TYPE: protein (xi) SEQUENCE DESCRIPTION: SEQ ID NO: 36:

```
Met Gly Trp Ser Cys Ile Ile Leu Phe Leu Val Ala Thr Ala Thr Gly
            -15                 -10                  -5

Val His Ser Gln Val Lys Leu Val Gln Ala Gly Gly Gly Val Val Gln
```

-continued

```
                 1               5                        10
Pro Gly Arg Ser Leu Arg Leu Ser Cys Ile Val Ser Gly Leu Ser Leu
                15                  20                  25

Thr Ser Asn Ser Val Asn Trp Ile Arg Gln Ala Pro Gly Lys Gly Leu
 30                  35                  40                  45

Glu Trp Val Ala Leu Ile Trp Ser Asn Gly Asp Thr Asp Tyr Asn Ser
                 50                  55                  60

Ala Ile Lys Ser Arg Phe Thr Ile Ser Arg Asp Asn Ser Lys Ser Thr
                 65                  70                  75

Leu Tyr Met Gln Met Asn Ser Leu Arg Thr Glu Asp Thr Ala Val Tyr
                 80                  85                  90

Phe Cys Ala Arg Glu Tyr Tyr Gly Tyr Phe Asp Tyr Trp Gly Gln Gly
                 95                 100                 105

Val Leu Val Thr Val Ser Ser
110                 115
```

(2) INFORMATION FOR SEQ ID NO: 37:

(i) SEQUENCE CHARACTERISTICS:
        (A) LENGTH:   127 amino acids
        (B) TYPE:     amino acid
        (D) TOPOLOGY: linear (ii) MOLECULE TYPE:   protein (xi) SEQUENCE DESCRIPTION: SEQ ID NO: 37:

```
Met Gly Trp Ser Cys Ile Ile Leu Phe Leu Val Ala Thr Ala Thr Gly
                -15                 -10                  -5

Val His Ser Asp Ile Gln Met Thr Gln Ser Pro Ser Ser Leu Ser Val
                  1                   5                  10

Ser Val Gly Asp Arg Val Thr Ile Thr Cys Leu Ala Ser Glu Gly Ile
                 15                  20                  25

Ser Ser Tyr Leu Ala Trp Tyr Gln Gln Lys Pro Gly Leu Ala Pro Lys
 30                  35                  40                  45

Leu Leu Ile Tyr Gly Ala Asn Ser Leu Gln Thr Gly Val Pro Ser Arg
                 50                  55                  60

Phe Ser Gly Ser Gly Ser Ala Thr Asp Phe Thr Leu Thr Ile Ser Ser
                 65                  70                  75

Leu Gln Pro Glu Asp Ile Ala Thr Tyr Tyr Cys Gln Gln Ser Tyr Lys
                 80                  85                  90

Phe Pro Asn Thr Phe Gly Gln Gly Thr Lys Val Asp Val Lys Arg
 95                 100                 105
```

(2) INFORMATION FOR SEQ ID NO: 38:

(i) SEQUENCE CHARACTERISTICS:
        (A) LENGTH:     42 base pairs
        (B) TYPE:       nucleic acid
        (C) STRANDEDNESS: single
        (D) TOPOLOGY:   linear (xi) SEQUENCE DESCRIPTION: SEQ ID NO: 38:

GATCTCTGCG ACTGAGTTGC ATCGCATCTG GGTTCACATT CT                42

(2) INFORMATION FOR SEQ ID NO: 39:

(i) SEQUENCE CHARACTERISTICS:
        (A) LENGTH:     42 base pairs
        (B) TYPE:       nucleic acid
        (C) STRANDEDNESS: single -continued (D) TOPOLOGY:    linear (xi) SEQUENCE DESCRIPTION: SEQ ID NO: 39:

CTAGAGAATG TGAACCCAGA TGCGATGCAA CTCAGTCGCA GA               42

(2) INFORMATION FOR SEQ ID NO: 40:

(i) SEQUENCE CHARACTERISTICS:
        (A) LENGTH:    135 amino acids
        (B) TYPE:    amino acid
        (D) TOPOLOGY:    linear (ii) MOLECULE TYPE:    protein (xi) SEQUENCE DESCRIPTION: SEQ ID NO: 40:

```
Met Gly Trp Ser Cys Ile Ile Leu Phe Leu Val Ala Thr Ala Thr Gly
            -15                 -10                  -5

Val His Ser Gln Val Lys Leu Val Gln Ala Gly Gly Gly Val Val Gln
             1               5                  10

Pro Gly Arg Ser Leu Arg Leu Ser Cys Ile Ala Ser Gly Phe Thr Phe
            15                  20                  25

Ser Ser Asn Ser Val Asn Trp Ile Arg Gln Ala Pro Gly Lys Gly Leu
 30              35                  40                  45

Glu Trp Val Ala Leu Ile Trp Ser Asn Gly Asp Thr Asp Tyr Asn Ser
                 50                  55                  60

Ala Ile Lys Ser Arg Phe Thr Ile Ser Arg Asp Asn Ser Lys Ser Thr
                 65                  70                  75

Leu Tyr Met Gln Met Asn Ser Leu Arg Thr Glu Asp Thr Ala Val Tyr
                 80                  85                  90

Phe Cys Ala Arg Glu Tyr Tyr Gly Tyr Phe Asp Tyr Trp Gly Gln Gly
 95                 100                 105

Val Leu Val Thr Val Ser Ser
110             115
```

(2) INFORMATION FOR SEQ ID NO: 41:

(i) SEQUENCE CHARACTERISTICS:
        (A) LENGTH:    127 amino acids
        (B) TYPE:    amino acid
        (D) TOPOLOGY:    linear (ii) MOLECULE TYPE:    protein (xi) SEQUENCE DESCRIPTION: SEQ ID NO: 41:

```
Met Gly Trp Ser Cys Ile Ile Leu Phe Leu Val Ala Thr Ala Thr Gly
            -15                 -10                  -5

Val His Ser Asp Ile Gln Met Thr Gln Ser Pro Ser Ser Leu Ser Val
             1               5                  10

Ser Val Gly Asp Arg Val Thr Ile Thr Cys Leu Ala Ser Glu Gly Ile
            15                  20                  25

Ser Ser Tyr Leu Ala Trp Tyr Gln Gln Lys Pro Gly Leu Ala Pro Lys
 30              35                  40                  45

Leu Leu Ile Tyr Gly Ala Asn Ser Leu Gln Thr Gly Val Pro Ser Arg
                 50                  55                  60

Phe Ser Gly Ser Gly Ser Ala Thr Asp Phe Thr Leu Thr Ile Ser Ser
                 65                  70                  75

Leu Gln Pro Glu Asp Ile Ala Thr Tyr Tyr Cys Gln Gln Ser Tyr Lys
                 80                  85                  90

Phe Pro Asn Thr Phe Gly Gln Gly Thr Lys Val Asp Val Lys Arg
```

-continued

```
                95                  100                  105
```

(2) INFORMATION FOR SEQ ID NO: 42:

(i) SEQUENCE CHARACTERISTICS:
        (A) LENGTH:   95 base pairs
        (B) TYPE:   nucleic acid
        (C) STRANDEDNESS:   single
        (D) TOPOLOGY:   linear (xi) SEQUENCE DESCRIPTION: SEQ ID NO: 42:

```
GCAGCTGCAG CCGCCACCAT GGGCTGGAGC TGTATCATCC TCTTCTTAGT AGCAACAGCT     60

ACAGGTGTCC ACTCCGAGGT CCAGCTGCTA GAGTC                                95
```

(2) INFORMATION FOR SEQ ID NO: 43:

(i) SEQUENCE CHARACTERISTICS:
        (A) LENGTH:   108 base pairs
        (B) TYPE:   nucleic acid
        (C) STRANDEDNESS:   single
        (D) TOPOLOGY:   linear (xi) SEQUENCE DESCRIPTION: SEQ ID NO: 43:

```
AGACGAATTC ACTAGTTAAT GATAACCCAG AGACTGCGCA ACTCAGTCGC AGAGATCCTC     60

CTGGCTGTAC GAGGCCACCT CCAGACTCTA GCAGCTGGAC CTCGGAGT                 108
```

(2) INFORMATION FOR SEQ ID NO: 44:

(i) SEQUENCE CHARACTERISTICS:
        (A) LENGTH:   103 base pairs
        (B) TYPE:   nucleic acid
        (C) STRANDEDNESS:   single
        (D) TOPOLOGY:   linear (xi) SEQUENCE DESCRIPTION: SEQ ID NO: 44:

```
AAGCGATCTA GAAATGACTC GAAGAACACC CTATACCTAC AGATGAACGG TCTGCAAGCT     60

GAAGTAAGTG CAATCTACTT CTGTGCTCGT GAGTACTATG GAT                      103
```

(2) INFORMATION FOR SEQ ID NO: 45:

(i) SEQUENCE CHARACTERISTICS:
        (A) LENGTH:   93 base pairs
        (B) TYPE:   nucleic acid
        (C) STRANDEDNESS:   single
        (D) TOPOLOGY:   linear (xi) SEQUENCE DESCRIPTION: SEQ ID NO: 45:

```
ACGAGAAGCT TCATGTCGAC GCTGAGGAGA CTGTGACTAG CGTACCTTGA CCCCAATAGT     60

CGAAATATCC ATAGTACTCA CGAGCACAGA AGT                                  93
```

(2) INFORMATION FOR SEQ ID NO: 46:

(i) SEQUENCE CHARACTERISTICS:
        (A) LENGTH:   135 amino acids
        (B) TYPE:   amino acid
        (D) TOPOLOGY:   linear (ii) MOLECULE TYPE:   protein (xi) SEQUENCE DESCRIPTION: SEQ ID NO: 46:

```
Met Gly Trp Ser Cys Ile Ile Leu Phe Leu Val Ala Thr Ala Thr Gly
            -15                 -10                  -5

Val His Ser Glu Val Gln Leu Leu Glu Ser Gly Gly Gly Leu Val Gln
  1               5                   10
```

```
Pro Gly Gly Ser Leu Arg Leu Ser Cys Ala Val Ser Gly Leu Ser Leu
         15                  20                  25

Thr Ser Asn Ser Val Asn Trp Ile Arg Gln Ala Pro Gly Lys Gly Leu
 30              35                  40                  45

Glu Trp Val Ala Leu Ile Trp Ser Asn Gly Asp Thr Asp Tyr Asn Ser
                 50                  55                  60

Ala Ile Lys Ser Arg Phe Thr Ile Ser Arg Asn Asp Ser Lys Asn Thr
                 65                  70                  75

Leu Tyr Leu Gln Met Asn Gly Leu Gln Ala Glu Val Ser Ala Ile Tyr
             80                  85                  90

Phe Cys Ala Arg Glu Tyr Tyr Gly Tyr Phe Asp Tyr Trp Gly Gln Gly
         95                 100                 105

Thr Leu Val Thr Val Ser Ser
110                 115
```

(2) INFORMATION FOR SEQ ID NO: 47:

(i) SEQUENCE CHARACTERISTICS:
        (A) LENGTH: 127 amino acids
        (B) TYPE: amino acid
        (D) TOPOLOGY: linear (ii) MOLECULE TYPE: protein (xi) SEQUENCE DESCRIPTION: SEQ ID NO: 47:

```
Met Gly Trp Ser Cys Ile Ile Leu Phe Leu Val Ala Thr Ala Thr Gly
            -15                 -10                  -5

Val His Ser Asp Ile Gln Met Thr Gln Ser Pro Ser Ser Leu Ser Val
             1                   5                  10

Ser Val Gly Asp Arg Val Thr Ile Thr Cys Leu Ala Ser Glu Gly Ile
         15                  20                  25

Ser Ser Tyr Leu Ala Trp Tyr Gln Gln Lys Pro Gly Leu Ala Pro Lys
 30              35                  40                  45

Leu Leu Ile Tyr Gly Ala Asn Ser Leu Gln Thr Gly Val Pro Ser Arg
                 50                  55                  60

Phe Ser Gly Ser Gly Ser Ala Thr Asp Phe Thr Leu Thr Ile Ser Ser
                 65                  70                  75

Leu Gln Pro Glu Asp Ile Ala Thr Tyr Tyr Cys Gln Gln Ser Tyr Lys
             80                  85                  90

Phe Pro Asn Thr Phe Gly Gln Gly Thr Lys Val Asp Val Lys Arg
         95                 100                 105
```

(2) INFORMATION FOR SEQ ID NO: 48:

(i) SEQUENCE CHARACTERISTICS:
        (A) LENGTH: 97 base pairs
        (B) TYPE: nucleic acid
        (C) STRANDEDNESS: single
        (D) TOPOLOGY: linear (xi) SEQUENCE DESCRIPTION: SEQ ID NO: 48:

```
gctgactgca gccgccacca tgggctggag ctgtatcatc ctcttcttag tagcaacagc    60
tacaggtgtc cactcccagg tcaaactggt acaagct                             97
```

(2) INFORMATION FOR SEQ ID NO: 49:

(i) SEQUENCE CHARACTERISTICS:
        (A) LENGTH: 108 base pairs
        (B) TYPE: nucleic acid

```
        (C) STRANDEDNESS:  single
        (D) TOPOLOGY:  linear (xi) SEQUENCE DESCRIPTION: SEQ ID NO: 49:

CTAGAAGCTT ACTAGTTAAT GATAACCCAG ATGCGATGCA ACTCAGTCGC AGAGATCTTC      60

CTGGCTGTAC GACGCCACCT CCAGCTTGTA CCAGTTTGAC CTGGGAGT                  108

(2) INFORMATION FOR SEQ ID NO: 50:

(i) SEQUENCE CHARACTERISTICS:
        (A) LENGTH:   90 base pairs
        (B) TYPE:   nucleic acid
        (C) STRANDEDNESS:  single
        (D) TOPOLOGY:  linear (xi) SEQUENCE DESCRIPTION: SEQ ID NO: 50:

GGACGAATTC ACTAGTAATG GTATGCACTG GGTACGGCAA GCACCTGGCA AGGGTCTGGA      60

GTGGGTTGCA GTAATATGGA GTAATGGATC                                      90

(2) INFORMATION FOR SEQ ID NO: 51:

(i) SEQUENCE CHARACTERISTICS:
        (A) LENGTH:   85 base pairs
        (B) TYPE:   nucleic acid
        (C) STRANDEDNESS:  single
        (D) TOPOLOGY:  linear (xi) SEQUENCE DESCRIPTION: SEQ ID NO: 51:

ACTGCTCTAG AGATTGTGAA TCGTCCTTTG ACTGAGTCAC CATAGTATGT TCGTGATCCA      60

TTACTCCATA TTACTGCAAC CCACT                                           85

(2) INFORMATION FOR SEQ ID NO: 52:

(i) SEQUENCE CHARACTERISTICS:
        (A) LENGTH:   95 base pairs
        (B) TYPE:   nucleic acid
        (C) STRANDEDNESS:  single
        (D) TOPOLOGY:  linear (xi) SEQUENCE DESCRIPTION: SEQ ID NO: 52:

CGTACTCTAG AGACAATTCG AAGCGCACCC TATACATGCA GATGAACAGT CTGAGAACTG      60

AAGATACTGC TGTCTACTAC TGTGCTCGTG AGTAC                                95

(2) INFORMATION FOR SEQ ID NO: 53:

(i) SEQUENCE CHARACTERISTICS:
        (A) LENGTH:   100 base pairs
        (B) TYPE:   nucleic acid
        (C) STRANDEDNESS:  single
        (D) TOPOLOGY:  linear (xi) SEQUENCE DESCRIPTION: SEQ ID NO: 53:

ACGAGAAGCT TCATGTCGAC GCTGAGGAGA CTGTGACTAG GACACCTTGA CCCCAATAGT      60

CGAAATATCC ATAGTACTCA CGAGCACAGT AGTAGACAGC                          100

(2) INFORMATION FOR SEQ ID NO: 54:

(i) SEQUENCE CHARACTERISTICS:
        (A) LENGTH:   153 base pairs
        (B) TYPE:   nucleic acid
        (C) STRANDEDNESS:  single
        (D) TOPOLOGY:  linear (xi) SEQUENCE DESCRIPTION: SEQ ID NO: 54:
```

```
GCGATAGGTC ACCATCACAT GTCAAGCAAG TGAGGGCATC TCCAGTTACT TAAACTGGTA        60

TCAGCAGAAG CCCGGGCTAG CTCCTAAGCT CCTGATCTAT GGTGCGAATA CCAGGGAGGC       120

TGGAGTACCA TCAAGATTCA GTGGCTCAGG CTC                                    153
```

(2) INFORMATION FOR SEQ ID NO: 55:

(i) SEQUENCE CHARACTERISTICS:
        (A) LENGTH:   150 base pairs
        (B) TYPE:   nucleic acid
        (C) STRANDEDNESS:   single
        (D) TOPOLOGY:   linear (xi) SEQUENCE DESCRIPTION: SEQ ID NO: 55:

```
ACAGTCGTCG ACCTTGGTGC CTTGACCGAA TGTGTTCGGG AACTTATACG ACTGTTGACA        60

GTAATACGTC GCGATATCTT CAGGCTGTAG GCTGGAGATC GTGAGCGTGA AGTCTGTACC       120

GGAGCCTGAG CCACTGAATC TTGATGGTAC                                        150
```

(2) INFORMATION FOR SEQ ID NO: 56:

(i) SEQUENCE CHARACTERISTICS:
        (A) LENGTH:   136 amino acids
        (B) TYPE:   amino acid
        (D) TOPOLOGY:   linear (ii) MOLECULE TYPE:   protein (xi) SEQUENCE DESCRIPTION: SEQ ID NO: 56:

```
Met Gly Trp Ser Cys Ile Ile Leu Phe Leu Val Ala Thr Ala Thr Gly
            -15                 -10                  -5

Val His Ser Gln Val Lys Leu Val Gln Ala Gly Gly Val Val Gln
              1               5                  10

Pro Gly Arg Ser Leu Arg Leu Ser Cys Ile Ala Ser Gly Leu Ser Leu
         15                  20                  25

Thr Ser Asn Gly Met His Trp Val Arg Gln Ala Pro Gly Lys Gly Leu
 30                  35                  40                  45

Glu Trp Val Ala Val Ile Trp Ser Asn Gly Ser Arg Thr Tyr Tyr Gly
                50                  55                  60

Asp Ser Val Lys Gly Arg Phe Thr Ile Ser Arg Asp Asn Ser Lys Arg
             65                  70                  75

Thr Leu Tyr Met Gln Met Asn Ser Leu Arg Thr Glu Asp Thr Ala Val
         80                  85                  90

Tyr Tyr Cys Ala Arg Glu Tyr Tyr Gly Tyr Phe Asp Tyr Trp Gly Gln
     95                 100                 105

Gly Val Leu Val Thr Val Ser Ser
110                 115
```

(2) INFORMATION FOR SEQ ID NO: 57:

(i) SEQUENCE CHARACTERISTICS:
        (A) LENGTH:   127 amino acids
        (B) TYPE:   amino acid
        (D) TOPOLOGY:   linear (ii) MOLECULE TYPE:   protein (xi) SEQUENCE DESCRIPTION: SEQ ID NO: 57:

```
Met Gly Trp Ser Cys Ile Ile Leu Phe Leu Val Ala Thr Ala Thr Gly
            -15                 -10                  -5

Val His Ser Asp Ile Gln Met Thr Gln Ser Pro Ser Ser Leu Ser Val
```

```
                 1               5                    10
Ser Val Gly Asp Arg Val Thr Ile Thr Cys Gln Ala Ser Glu Gly Ile
                15                  20                  25
Ser Ser Tyr Leu Asn Trp Tyr Gln Gln Lys Pro Gly Leu Ala Pro Lys
 30                  35                  40                  45
Leu Leu Ile Tyr Gly Ala Asn Thr Arg Glu Ala Gly Val Pro Ser Arg
                    50                  55                  60
Phe Ser Gly Ser Gly Ser Gly Thr Asp Phe Thr Leu Thr Ile Ser Ser
                65                  70                  75
Leu Gln Pro Glu Asp Ile Ala Thr Tyr Tyr Cys Gln Gln Ser Tyr Lys
                80                  85                  90
Phe Pro Asn Thr Phe Gly Gln Gly Thr Lys Val Asp Val Lys Arg
                95                 100                 105
```

(2) INFORMATION FOR SEQ ID NO: 58:

(i) SEQUENCE CHARACTERISTICS:
        (A) LENGTH:   98 base pairs
        (B) TYPE:     nucleic acid
        (C) STRANDEDNESS:  single
        (D) TOPOLOGY:  linear (xi) SEQUENCE DESCRIPTION: SEQ ID NO: 58:

```
GCATGACAGT AGATCTCTGC GACTGAGTTG CATCGCATCT GGGTTCACAT TCTCTAGTAA      60

TAGTGTGAAC TGGGTACGGC AAGCACCTGG CAAGGGTC                              98
```

(2) INFORMATION FOR SEQ ID NO: 59:

(i) SEQUENCE CHARACTERISTICS:
        (A) LENGTH:   113 base pairs
        (B) TYPE:     nucleic acid
        (C) STRANDEDNESS:  single
        (D) TOPOLOGY:  linear (xi) SEQUENCE DESCRIPTION: SEQ ID NO: 59:

```
ACGATCACTC TAGAGATTGT GAATCGAGAT TTGATAGCTG AATTATAATC TGTGTCTCCA      60

TTACTCCATA TTAGTGCAAC CCACTCCAGA CCCTTGCCAG GTGCTTGCCG TAC            113
```

(2) INFORMATION FOR SEQ ID NO: 60:

(i) SEQUENCE CHARACTERISTICS:
        (A) LENGTH:   91 base pairs
        (B) TYPE:     nucleic acid
        (C) STRANDEDNESS:  single
        (D) TOPOLOGY:  linear (xi) SEQUENCE DESCRIPTION: SEQ ID NO: 60:

```
GCATGGACGT CTAGAGACAA TTCGAAGAGA ACCCTATACA TGCAGATGAA CAGTCTGAGA      60

ACTGAAGATA CTGCAGTCTA CTACTGTGCT C                                     91
```

(2) INFORMATION FOR SEQ ID NO: 61:

(i) SEQUENCE CHARACTERISTICS:
        (A) LENGTH:   120 base pairs
        (B) TYPE:     nucleic acid
        (C) STRANDEDNESS:  single
        (D) TOPOLOGY:  linear (xi) SEQUENCE DESCRIPTION: SEQ ID NO: 61:

```
CAAGTCGACG ACAAGCTTGT CGACGCTGAG GAGACTGTGA CTAGGACACC TTGACCCCAA      60

TAGTCGAAAT ATCCATAGTA CTCACGAGCA CAGTAGTAGA CTGCAGTATC TTCAGTTCTC    120
```

(2) INFORMATION FOR SEQ ID NO: 62:

(i) SEQUENCE CHARACTERISTICS:
        (A) LENGTH:  28 base pairs
        (B) TYPE:  nucleic acid
        (C) STRANDEDNESS:  single
        (D) TOPOLOGY:  linear (xi) SEQUENCE DESCRIPTION: SEQ ID NO: 62:

ACAGTCCGTT TGACGTCGAC CTTGGTGC                                              28

(2) INFORMATION FOR SEQ ID NO: 63:

(i) SEQUENCE CHARACTERISTICS:
        (A) LENGTH:  63 base pairs
        (B) TYPE:  nucleic acid
        (C) STRANDEDNESS:  single
        (D) TOPOLOGY:  linear (xi) SEQUENCE DESCRIPTION: SEQ ID NO: 63:

AGTGGCTCAG GATCCGGTAC CGACTTCACG TTCACGATCT CCAGCCTACA GCCTGAAGAT          60

ATC                                                                         63

(2) INFORMATION FOR SEQ ID NO: 64:

(i) SEQUENCE CHARACTERISTICS:
        (A) LENGTH:  135 amino acids
        (B) TYPE:  amino acid
        (D) TOPOLOGY:  linear (ii) MOLECULE TYPE:  protein (xi) SEQUENCE DESCRIPTION: SEQ ID NO: 64:

Met Gly Trp Ser Cys Ile Ile Leu Phe Leu Val Ala Thr Ala Thr Gly
             -15                 -10                 -5

Val His Ser Gln Val Lys Leu Val Gln Ala Gly Gly Val Val Gln
              1               5                  10

Pro Gly Arg Ser Leu Arg Leu Ser Cys Ile Ala Ser Gly Phe Thr Phe
     15                  20                  25

Ser Ser Asn Ser Val Asn Trp Val Arg Gln Ala Pro Gly Lys Gly Leu
 30              35                  40                  45

Glu Trp Val Ala Leu Ile Trp Ser Asn Gly Asp Thr Asp Tyr Asn Ser
             50                  55                  60

Ala Ile Lys Ser Arg Phe Thr Ile Ser Arg Asp Asn Ser Lys Arg Thr
             65                  70                  75

Leu Tyr Met Gln Met Asn Ser Leu Arg Thr Glu Asp Thr Ala Val Tyr
         80                  85                  90

Tyr Cys Ala Arg Glu Tyr Tyr Gly Tyr Phe Asp Tyr Trp Gly Gln Gly
     95                 100                 105

Val Leu Val Thr Val Ser Ser
110                 115

(2) INFORMATION FOR SEQ ID NO: 65:

(i) SEQUENCE CHARACTERISTICS:
        (A) LENGTH:  127 amino acids
        (B) TYPE:  amino acid
        (D) TOPOLOGY:  linear (ii) MOLECULE TYPE:  protein (xi) SEQUENCE DESCRIPTION: SEQ ID NO: 65:

```
Met Gly Trp Ser Cys Ile Ile Leu Phe Leu Val Ala Thr Ala Thr Gly
            -15              -10                  -5

Val His Ser Asp Ile Gln Met Thr Gln Ser Pro Ser Ser Leu Ser Val
            1            5                   10

Ser Val Gly Asp Arg Val Thr Ile Thr Cys Leu Ala Ser Glu Gly Ile
        15              20              25

Ser Ser Tyr Leu Ala Trp Tyr Gln Gln Lys Pro Gly Leu Ala Pro Lys
30                  35              40                      45

Leu Leu Ile Tyr Gly Ala Asn Ser Leu Gln Thr Gly Val Pro Ser Arg
                50              55                  60

Phe Ser Gly Ser Gly Ser Gly Thr Asp Phe Thr Phe Thr Ile Ser Ser
            65              70              75

Leu Gln Pro Glu Asp Ile Ala Thr Tyr Tyr Cys Gln Gln Ser Tyr Lys
        80              85              90

Phe Pro Asn Thr Phe Gly Gln Gly Thr Lys Val Asp Val Lys Arg
        95              100             105

(2) INFORMATION FOR SEQ ID NO: 66:

(i) SEQUENCE CHARACTERISTICS:
        (A) LENGTH:    40 base pairs
        (B) TYPE:    nucleic acid
        (C) STRANDEDNESS:    single
        (D) TOPOLOGY:    linear (xi) SEQUENCE DESCRIPTION: SEQ ID NO: 66:

AGCGAGCGCT CGAGGTCAAA CGGACTGTGG CTGCACCATC                                40
```

HUMANIZED MONOCLONAL ANTIBODIES AGAINST HUMAN INTERLEUKIN-5

This is a U.S. national phase application of PCT/US93/00759, filed Feb. 4, 1993, which is a continuation-in-part of U.S. application Ser. No. 07/832,842, filed Feb. 6, 1992, now abandoned.

The invention relates to nucleic acids which encode the heavy and light chain variable regions of a monoclonal antibody against human interleukin-5 and complementarity determining regions therefrom, and to humanized antibodies and binding proteins based upon the monoclonal antibody.

BACKGROUND OF THE INVENTION

Interleukin-5 (IL-5) is a lymphokine secreted by activated T cells which is biologically active on B cells and eosinophils. Because IL-5 replaces T lymphocytes in in vitro antibody responses to thymus-dependent antigens, it was formerly called T cell replacing factor [TRF; Dutton et al., Prog. Immunol. 1:355 (1971); Schimpl et al., Nature 237:15 (1972)]. Because it also stimulates differentiation of B lymphocytes into IgM and IgG plaque-forming cells and the growth of B cell lymphomas in vitro, it has also been called B cell growth factor II [BCGFII; Takatsu et al., J Immunol. 124:2414 (1980)].

Murine IL-5 consists of 133 amino acid residues, including a signal sequence of 20 residues and three potential N-glycosylation sites. Deglycosylation does not affect the biological activity of murine IL-5 in a B cell proliferation assay [Tavernier et al., DNA 8:491 (1989)]. Human IL-5 consists of 134 amino acid residues, including a signal sequence of 19 residues and two potential N-glycosylation sites. The structures of both proteins have been described by Yokota et al. [Proc. Natl. Acad. Sci. USA 84:7388 (1987)] and Kinashi et al. [Nature 324:70 (1986)]. The degrees of homology of murine and human IL-5 at the nucleotide and amino acid sequence level are 77 and 70%, respectively.

Both murine and human IL-5 exist as homodimers linked by disulfide bonds. Therefore, glycosylated recombinant human IL-5 migrates in SDS polyacrylamide gel electrophoresis with an apparent molecular weight of 40,000 daltons under non-reducing conditions, and 20–22,000 daltons under reducing conditions [Tsujimoto et al., J. Biochem. 106:23 (1989)].

The cloning and expression of murine IL-5 has been described, e.g., by Kinashi et al. [Nature 324:70 (1986)] and Takatsu et al. [J. Immunol. 134:382 (1985)]. Human IL-5 complementary DNA (cDNA) has been isolated using murine IL-5 cDNA as a probe by Azuma et al. [Nucleic Acids Res. 14:9149 (1986)].

IL-5 has been shown to act as a maintenance and differentiation factor for eosinophils. In humans, the activity of IL-5 appears to be specific, affecting eosinophils primarily. Human IL-5 induces eosinophil precursor cells to become mature cells. Moreover, the survival of eosinophils isolated from circulating blood can be prolonged when human IL-5 is present in the culture media. Human IL-5 also stimulates cultured eosinophils to degranulate, and to release toxic proteins such as major basic protein (MBP) and eosinophil-derived neurotoxin (EDN) [Kita et al., J. Immunol. 149:629 (1992)].

It has been suggested that eosinophils kill parasites following infection and also play a significant role in inflammatory and allergic diseases [see, e.g., Sanderson, Blood 79:3101 (1992)]. Increased levels of eosinophils among circulating leukocytes have been observed following parasitic infections and in certain chronic inflammatory tissues, such as in asthmatic alveoli. Eosinophil infiltration and toxic granule release from eosinophils may play a role in tissue destruction and may aggravate the symptoms of asthma.

For example, Gleich et al. [Adv. Immunol. 39:177 (1986)] and Frigas et al. [J. Allergy Clin. Immunol. 77:527 (1986)] have shown that high-density eosinophils and eosinophil major basic protein (MBP) are associated with bronchial asthma and related tissue damage.

Recently, Coffman et al. (International Patent Application Publication No. WO90/04979) have shown that antibodies against IL-5 can prevent or reduce eosinophilia which is associated with certain allergic diseases such as asthma. Monoclonal antibodies which specifically bind to and neutralize the biological activity of human IL-5 can be used for this purpose.

A monoclonal antibody against IL-5 has been reported to have a prominent effect in reversing parasite-induced eosinophilia in experimental animals [Schumacher et al, J. Immunol. 141:1576 (1988); Coffman et. al., Science 245:308 (1989)], suggesting that neutralizing antibodies may be clinically useful in relieving eosinophilia-related symptoms by antagonizing IL-5. In fact, it has been reported that when rodents or monkeys bearing experimentally induced eosinophilia were treated with TRFK 5, a rat anti-mouse IL-5 monoclonal antibody, eosinophil counts in both circulation and bronchial lavage were found to return to normal levels. Thus, neutralizing monoclonal antibodies may be effective antagonists.

Because most monoclonal antibodies are of rodent origin, however, there is an increased likelihood that they would be immunogenic if used therapeutically in a human being, particularly over a long period of time. To reduce this possibility, there is a need for recombinant or "humanized" antibodies against human IL-5. Such antibodies could be used for the treatment of conditions associated with eosinophilia, or for the treatment of any other condition attributable to the biological activity of IL-5.

Initial efforts to reduce the immunogenicity of rodent antibodies involved the production of chimeric antibodies, in which mouse variable regions were fused with human constant regions [Liu et al., Proc. Natl. Acad. Sci. USA 84:3439 (1987)]. It has been shown, however, that mice injected with hybrids of human variable regions and mouse constant regions develop a strong anti-antibody response directed against the human variable region. This suggests that in the human system, retention of the entire rodent Fv region in such chimeric antibodies may still give rise to human anti-mouse antibodies.

It is generally believed that CDR loops of variable domains comprise the binding site of antibody molecules, the grafting of rodent CDR loops onto human frameworks (i.e., humanization) was attempted to further minimize rodent sequences [Jones et al., Nature 321:522 (1986); Verhoeyen et al., Science 239:1534 (1988)]. Studies by Kabat et al. [J. Immunol. 147:1709 (1991)] have shown that framework residues of antibody variable domains are involved in CDR loop support. It has also been found that changes in framework support residues in humanized antibodies may be required to preserve antigen binding affinity. The use of CDR grafting and framework residue preservation in a number of humanized antibody constructs has been reported, e.g., by Queen et al. [Proc. Natl. Acad. Sci. USA 86:10029 (1989)], Gorman et al. [Proc. Natl. Acad. Sci. USA 88:4181 (1991)] and Hodgson [Bio/Technology 9:421 (1991)]. Exact sequence information has been reported for only a few humanized constructs.

Although a high degree of sequence identity between human and animal antibodies has been known to be important in selecting human antibody sequences for humanization, most prior studies have used a different human sequence for animal light and heavy variable sequences. Sequences of known antibodies have been used or, more typically, those of antibodies having known X-ray structures, antibodies NEW and KOL. See, e.g., Jones et al., supra; Verhoeyen et al., supra; and Gorman et al., supra.

Methods for engineering antibodies have been described, e.g., by Boss et al. (U.S. Pat. No. 4,816,397), Cabilly et al. (U.S. Pat. No. 4,816,567), Law et al. (European Patent Application Publication No. 438 310) and Winter (European Patent Application Publication No. 239 400).

Reliance on the relatively few antibodies for which X-ray structures have been determined has led to the frequent use of different human light and heavy chain sequences from different antibodies, because although only two human Fab crystal structures are known, several human light chain crystal structures have been determined. Such an approach may require changing framework residues in the human heavy and light chains to ensure correct chain association and, therefore, limits the applicability of humanization.

There thus is a need for improved methods for making humanized antibodies that are not based upon the relatively few known crystallographic structures.

SUMMARY OF THE INVENTION

The present invention fulfills the foregoing needs by providing novel methods for the design of humanized antibodies, and specific antibody antagonists of human IL-5 and pharmaceutical compositions containing the same.

More particularly, this invention provides a method for selecting human antibody sequences to be used as human frameworks for humanization of an animal antibody comprising:

(a) comparing the heavy and light chain variable region sequences of an animal monoclonal antibody that is to be humanized with optimally-aligned sequences of the heavy and light chain variable regions of human antibodies for which sequence information is available, thereby determining the percent identities for each of the compared sequences;

(b) determining the number of ambiguities in each of such human antibody sequences;

(c) comparing Pin-region spacing of the animal antibody sequences with (i) that of each of such human antibody sequences and with (ii) those of other antibodies which have known 3-dimensional structures; and (d) selecting the human antibody sequence which has the best combination of:

(i) low number of sequence ambiguities, and (ii) high percent identities and similar Pin-region spacing, based on comparison to the animal antibody sequences.

This invention further provides a method for determining which variable region residues of an animal monoclonal antibody should be selected for humanization comprising:

(a) determining potential minimal and maximal residues of the animal monoclonal antibody, wherein:

(i) such minimal residues comprise CDR structural loops plus residues required to support and/or orient the CDR structural loops, and (ii) such maximal residues comprise Kabat CDRs plus CDR structural loops plus residues required to support and/or orient the CDR structural loops plus residues which fall within about 10 Å of a CDR structural loop and possess a water solvent accessible surface of about 5 Å$^2$ or greater;

(b) performing computer modeling of:

(i) a sequence of an animal monoclonal antibody which is to be humanized, (ii) a human antibody framework sequence, and (iii) all possible recombinant antibodies comprising the human antibody framework sequence into which the minimal and maximal residues of step (a) have been inserted, which computer modeling is performed using software suitable for protein modeling and structural information from a structurally-characterized antibody that has a sequence most nearly identical to that of the selected human antibody framework sequence;

(c) comparing results obtained in the computer modeling of step (b); and (d) selecting the minimal or maximal residues which produce a recombinant antibody having a computer-modeled structure closest to that of the animal monoclonal antibody.

Preferably, the human antibody framework sequence is selected as described above.

The present invention still further provides a monoclonal antibody produced by a hybridoma having the identifying characteristics of a cell line deposited under American Type Culture Collection Accession No. ATCC HB 10959, and the hybridoma itself.

This invention still further provides polypeptides comprising a heavy or light chain variable region of a monoclonal antibody which have amino acid sequences defined by SEQ ID NO: 1 and SEQ ID NO: 2, complementarity determining regions (CDRs) from such variable regions, and isolated DNAs encoding such variable regions and CDRs. These DNAs can be used to construct binding compositions, single-chain binding proteins, polypeptides which contain one or more of the CDRs and retain antigen binding activity, and recombinant antibodies comprising such CDRs, all of which are a part of this invention.

This invention still further provides pharmaceutical compositions comprising such monoclonal antibody or recombinant antibodies, binding compositions, single-chain binding proteins and polypeptides; and a physiologically acceptable carrier.

BRIEF DESCRIPTION OF THE FIGURES

The present invention may be more readiy understood by reference to the description and example below, and to the accompanying figures in which.

DESCRIPTION OF THE INVENTION

Figure 1:
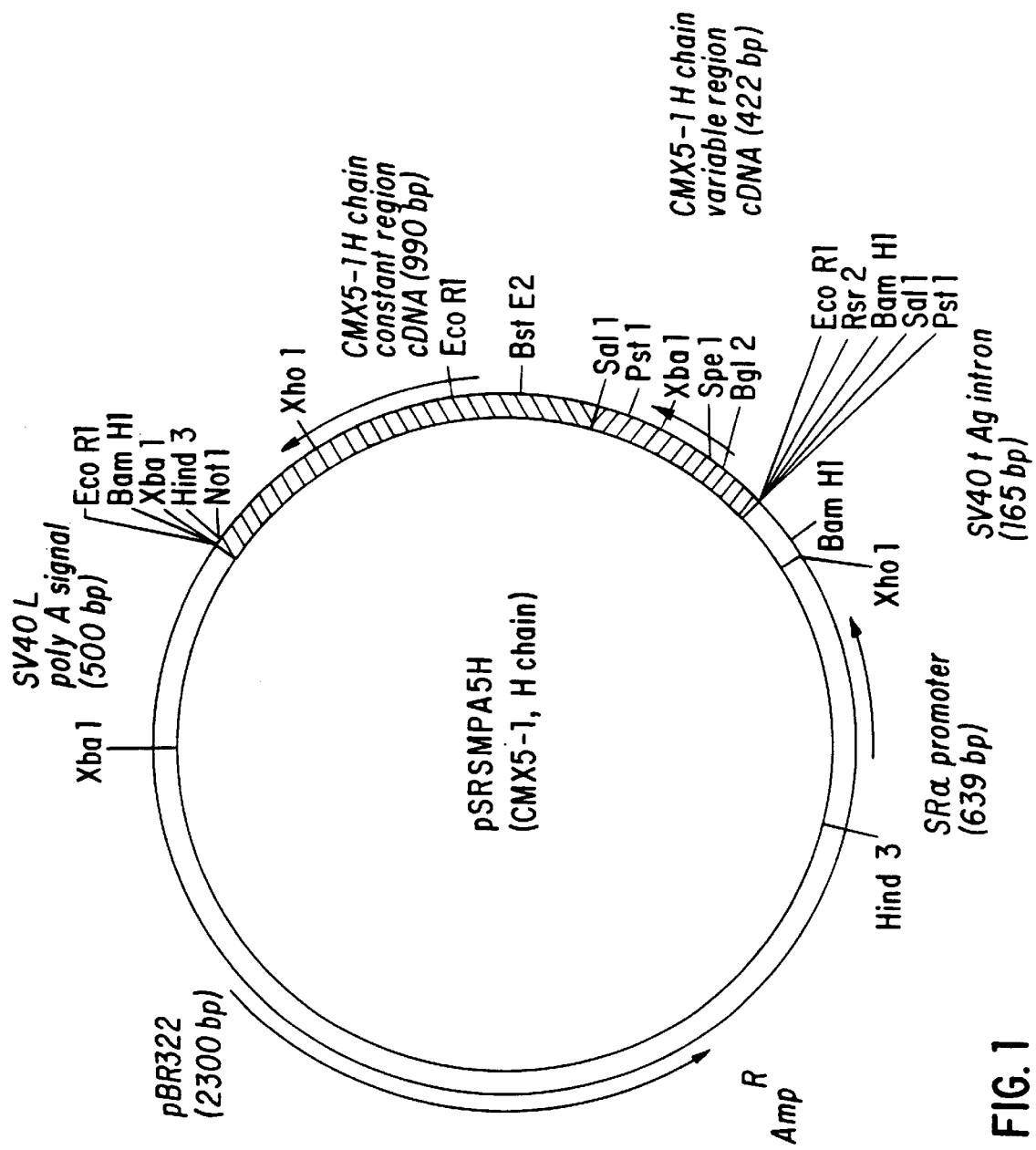
FIG. 1 is a schematic representation of plasmid pSRSMPA5H.

All references cited herein are hereby incorporated in their entirety by reference.

As used herein, the terms "DNA" and "DNAs" are defined as molecules comprising deoxyribonucleotides linked in standard 5' to 3' phosphodiester linkage, including both smaller oligodeoxyribonucleotides and larger deoxyribonucleic acids.

Antibodies comprise an assembly of polypeptide chains linked together by disulfide bridges. Two principal polypeptide chains, referred to as the light chain and the heavy chain, make up all major structural classes (isotypes) of antibody. Both heavy chains and light chains are further divided into sub regions referred to as variable regions and constant regions. Heavy chains comprise a single variable region and three or four different constant regions, and light chains comprise a single variable region (different from that of the heavy chain) and a single constant region (different from those of the heavy chain). The variable regions of the heavy chain and light chain are responsible for the antibody's binding specificity.

As used herein, the term "CDR structural loops" means the three light chain and the three heavy chain regions in the variable portion of an antibody that bridge β strands on the binding portion of the molecule. These loops have characteristic canonical structures [Chothia et al., *J. Mol. Biol.* 196:901 (1987); Chothia et al., *J. Mol. Biol.* 227:799 (1992)].

The term "Kabat CDRs" refers to hypervariable antibody sequences on heavy and light chains as defined by Kabat et al. [*Sequences of Proteins of Immunological Interest*, 4th Edition, 1987, U.S. Department of Health and Human Services, National Institutes of Health].

As used herein, the term "heavy chain variable region" means a polypeptide which is from about 110 to 125 amino acid residues in length, the amino acid sequence of which corresponds to that of a heavy chain of a monoclonal antibody of the invention, starting from the amino-terminal (N-terminal) amino acid residue of the heavy chain. Likewise, the term "light chain variable region" means a polypeptide which is from about 95 to 130 amino acid residues in length, the amino acid sequence of which corresponds to that of a light chain of a monoclonal antibody of the invention, starting from the N-terminal amino acid residue of the light chain.

The terms Fab, Fc, F(ab)$_2$, and Fv are employed with their standard immunological meanings [Klein, *Immunology* (John Wiley, New York, 1982); Parham, Chapter 14, in Weir, ed. *Immunochemistry*, 4th Ed. (Blackwell Scientific Publishers, Oxford, 1986)].

As used herein the term "monoclonal antibody" refers to a homogeneous population of immunoglobulins which are capable of specifically binding to human IL-5. It is understood that human IL-5 may have one or more antigenic determinants comprising (1) peptide antigenic determinants which consist of single peptide chains within human IL-5, (2) conformational antigenic determinants which consist of more than one spatially contiguous peptide chains whose respective amino acid sequences are located disjointedly along the human IL-5 polypeptide sequence; and (3) post-translational antigenic determinants which consist, either in whole or part, of molecular structures covalently attached to human IL-5 after translation, such as carbohydrate groups, or the like. The antibodies of the invention may be directed against one or more of these determinants.

As used herein the term "binding composition" means a composition comprising two polypeptide chains (1) which, when operationally associated, assume a conformation having high binding affinity for human IL-5, and (2) which are derived from a hybridoma producing monoclonal antibodies specific for human IL-5. The term "operationally associated" is meant to indicate that the two polypeptide chains can be positioned relative to one another for binding by a variety of means, including association in a native antibody fragment, such as Fab or Fv, or by way of genetically engineered cysteine-containing peptide linkers or other linkers at the carboxyl termini.

Monoclonal antibodies can be prepared using standard methods, e.g., as described by Kohler et al. [*Nature* 256:495 (1975); *Eur. J. Immunol.* 6:511 (1976)]. Essentially, an animal is immunized by standard methods to produce antibody-secreting somatic cells. These cells are then removed from the immunized animal for fusion to myeloma cells.

Somatic cells with the potential to produce antibodies, particularly B cells, are suitable for fusion with a myeloma cell line. These somatic cells may be derived from the lymph nodes, spleens and peripheral blood of primed animals. In the exemplary embodiment of this invention rat spleen cells are used, in part because these cells produce a relatively high percentage of stable fusions with mouse myeloma lines. It would be possible, however, to use human, mouse, rabbit, sheep or goat cells, or cells from other animal species instead.

Specialized myeloma cell lines have been developed from lymphocytic tumors for use in hyridoma-producing fusion procedures [Kohler and Milstein, *Eur. J. Immunol.* 6:511 (1976); Shulman el al., *Nature* 276:269 (1978); Volk et al., *J. Virol.* 42:220 (1982)]. These cell lines have been developed for at least three reasons. The first is to facilitate the selection of fused hybridomas from unfused and similarly indefinitely self-propagating myeloma cells. Usually, this is accomplished by using myelomas with enzyme deficiencies that render them incapable of growing in certain selective media that support the growth of hybridomas. The second reason arises from the inherent ability of lymphocytic tumor cells to produce their own antibodies. The purpose of using monoclonal techniques is to obtain fused hybrid cell lines with unlimited life spans that produce the desired single antibody under the genetic control of the somatic cell component of the hybridoma. To eliminate the production of tumor cell antibodies by the hybridomas, myeloma cell lines incapable of producing endogenous light or heavy immunoglobulin chains are used. A third reason for selection of these cell lines is for their suitability and efficiency for fusion.

Many myeloma cell lines may be used for the production of fused cell hybrids, including, e.g., P3X63-Ag8, P3X63-AG8.653, P3/NS1-Ag4-1 (NS-1), Sp2/0-Ag14 and S194/5.XXO.Bu.1. The P3X63-Ag8 and NS-1 cell lines have been described by Kohler and Milstein [*Eur. J. Immunol.* 6:511 (1976)]. Shulman et al. [*Nature* 276:269 (1978)) developed the Sp2/0-Ag14 myeloma line. The S194/5.XXO.Bu.1 line was reported by Trowbridge [*J. Exp. Med.* 148:313 (1979)].

Methods for generating hybrids of antibody-producing spleen or lymph node cells and myeloma cells usually involve mixing somatic cells with myeloma cells in a 10:1 proportion (although the proportion may vary from about 20:1 to about 1:1), respectively, in the presence of an agent or agents (chemical, viral or electrical) that promotes the fusion of cell membranes. Fusion methods have been described by Kohler and Milstein, supra, Gefter et al. [*Somatic Cell Genet.* 3:231 (1977)], and Volk et al. (*J. Virol.* 42:220 (1982)]. The fusion-promoting agents used by those investigators were Sendai virus and polyethylene glycol (PEG).

Because fusion procedures produce viable hybrids at very low frequency (e.g., when spleens are used as a source of somatic cells, only one hybrid is obtained for roughly every $1 \times 10^5$ spleen cells), it is essential to have a means of selecting the fused cell hybrids from the remaining unfused cells, particularly the unfused myeloma cells. A means of detecting the desired antibody-producing hybridomas among other resulting fused cell hybrids is also necessary.

Generally, the selection of fused cell hybrids is accomplished by culturing the cells in media that support the growth of hybridomas but prevent the growth of the unfused myeloma cells, which normally would go on dividing indefinitely. The somatic cells used in the fusion do not maintain long-term viability in in vitro culture and hence do not pose a problem. In the example of the present invention, myeloma cells lacking hypoxanthine phosphoribosyl transferase (HPRT-negative) were used. Selection against these cells is made in hypoxanthine/aminopterin/thymidine (HAT) medium, a medium in which the fused cell hybrids survive due to the HPRT-positive genotype of the spleen cells. The use of myeloma cells with different genetic deficiencies (drug sensitivities, etc.) that can be selected against in media supporting the growth of genotypically competent hybrids is also possible.

Several weeks are required to selectively culture the fused cell hybrids. Early in this time period, it is necessary to identify those hybrids which produce the desired antibody, so that they may subsequently be cloned and propagated. Generally, around 10% of the hybrids obtained produce the desired antibody, although a range of from about 1 to about 30% is not uncommon. The detection of antibody-producing hybrids can be achieved by any one of several standard assay methods, including enzyme-linked immunoassay and radio-immunoassay techniques which have been described in the literature [see, e.g., Kennet et al. (editors), Monoclonal Antibodies and Hybridomas: A New Dimension in Biological Analyses, pp. 376–384, Plenum Press, New York (1980)].

Once the desired fused cell hybrids have been selected and cloned into individual antibody-producing cell lines, each cell line may be propagated in either of two standard ways. A suspension of the hybridoma cells can be injected into a histocompatible animal. The injected animal will then develop tumors that secrete the specific monoclonal antibody produced by the fused cell hybrid. The body fluids of the animal, such as serum or ascites fluid, can be tapped to provide monoclonal antibodies in high concentration. Alternatively, the individual cell lines may be propagated in vitro in laboratory culture vessels. The culture medium containing high concentrations of a single specific monoclonal antibody can be harvested by decantation, filtration or centrifugation, and subsequently purified.

Monoclonal antibodies can also be produced using well known phage library systems.

The use and generation of fragments of antibodies is well known, e.g., Fab fragments [Tijssen, *Practice and Theory of Enzyme Immunoassays* (Elsevier, Amsterdam, 1985)], Fv fragments [Hochman et al., Biochemistry 12:1130 (1973); Sharon et al., *Biochemistry* 15:1591 (1976); Ehrlich et al., U.S. Pat. No. 4,355,023] and antibody half molecules (Auditore-Hargreaves, U.S. Pat. No. 4,470,925). Moreover, such compounds and compositions of the invention can be used to construct bi-specific antibodies by known techniques, e.g., by further fusions of hybridomas (i.e. to form so-called quadromas; Reading, U.S. Pat. No. 4,474,493) or by chemical reassociation of half molecules [Brennan et al., Science 229:81 (1985)].

Hybridomas and monoclonal antibodies can be produced against human IL-5 from any source, e.g., from commercial or natural sources or through the application of chemical synthetic methods or recombinant DNA technology. "Recombinant IL-5" is defined herein to mean IL-5 produced by expression of recombinant DNA (cDNA) encoding the same in a prokaryotic or eukaryotic expression system. In addition, genomic DNA can be used for producing IL-5 in eukaryotic systems. The IL-5 produced may be glycosylated or unglycosylated.

Since the nucleotide sequences of DNA encoding murine and human IL-5 are known [see e.g., Azuma et al., *Nucleic Acids Res.* 14:9149 (1986)], such DNAs can be chemically synthesized using the phosphoramidite solid support method of Matteucci et al. [*J. Am. Chem. Soc.* 103:3185 (1981)], the method of Yoo et al. [*J. Biol. Chem.* 764:17078 (1989)], or other well known methods. This can be done, for example, by synthesizing relatively small oligonucleotides and ligating them together, analogous to the way that Barr et al. (International Patent Application Publication No. WO 85/02200) chemically synthesized DNA encoding IL-2.

Alternatively, a cell line capable of making IL-5 can be stimulated to make IL-5 mRNA, which can serve as a template to make IL-5 cDNA by standard methods. A cDNA library can then be constructed in which IL-5 cDNA can be identified using oligonucleotide probe mixtures based on the known sequence information. This cDNA can then be cloned and expressed in one of the many available bacterial, yeast or mammalian expression systems. This method has been used to produce recombinant rat, mouse or human IL-5 [see, e.g., Tavernier et al., *DNA* 8:491 (1989); Minamitake et al., *J. Biochem.* 107:292 (1990); Uberla et al., Cytokine 3:72 (1991)]. Human IL-5 was produced in a commonly-owned U.S. patent application (Ser. No. 07/615,061, filed Nov. 16, 1990) by expressing cDNA encoding human IL-5 in Chinese hamster ovary (CHO) cells. Tsujimoto et al. [*J. Biochem.* 106:23 (1989)] have also described the production of recombinant human IL-5 in CHO cells.

In still another approach, oligonucleotide probe mixtures based on known IL-5 nucleotide sequences can be used to identify IL-5 genes in genomic DNA libraries prepared by standard methods. DNA thus identified can be excised from the library by restriction endonuclease cleavage, sequenced and expressed in a eukaryotic expression system or (following intron deletion by standard methods if necessary) in a prokaryotic expression system. In this way, Campbell et al. [*Proc. Natl. Acad. Sci. USA* 84:6629 (1987)] produced human IL-5 in monkey kidney (COS) cells.

Of course, both cDNA and genomic DNA libraries can be screened by the application of standard expression cloning methods, instead of by the use of oligonucleotide probes. IL-5 thus produced is detected through the use of known immunochemical or bioassay methods.

IL-5 polypeptides can also be made directly using synthetic peptide chemistry, e.g., as described by Merrifield [*J. Am. Chem. Soc.* 85:2149 (1963)], or IL-5 can be purchased commercially.

Once a hybridoma producing the desired monoclonal antibody is obtained, techniques can be used to produce interspecific monoclonal antibodies wherein the binding region of one species is combined with a non-binding region of the antibody of another species [Liu et al., *Proc. Natl. Acad. Sci. USA* 84:3439 (1987)]. For example, the CDRs from a rodent monoclonal antibody can be grafted onto a human antibody, thereby "humanizing" the rodent antibody [Riechmann et al., *Nature* 332:323 (1988)]. More particularly, the CDRs can be grafted onto a human antibody variable region with or without human constant regions.

Such methodology has been used, e.g., to humanize a mouse monoclonal antibody against the p55 (Tac) subunit of the human interleukin-2 receptor [Queen et al., *Proc. Natl. Acad. Sci. USA* 86:10029 (1989)].

The cDNAs of the present invention which encode the heavy and light chain variable regions of monoclonal antibodies specific for human IL-5 and the CDRs from such antibodies can be engineered in such a fashion. The location of the CDRs within the variable regions of the antibodies can be determined using a number of well known standard methods. For example, Kabat et al., supra, have published rules for locating CDRs. CDRs determined using these rules are referred to herein as "Kabat CDRs." Computer programs are also available which can be used to identify CDR structural loops on the basis of the amino acid residues involved in the three-dimensional binding site loops of the antibody chains, e.g., as described below.

The methods used herein are applicable to the humanization of a wide variety of animal antibodies. A two-step approach is used which involves (a) selecting human antibody sequences that are used as human frameworks for humanization, and (b) determining which variable region residues of an animal monoclonal antibody should be selected for insertion into the human framework chosen.

The first step involves selection of the best available human framework sequences for which sequence information is available. This selection process is based upon the following selection criteria:

(1) Percent Identities

The sequences of the heavy and light chain variable regions of an animal monoclonal antibody that is to be humanized are optimally aligned and compared preferably with all known human antibody heavy and light chain variable region sequences. This is in contrast to the methods of the prior art, which rely heavily on the use of only two human antibodies, NEW and KOL. Structural information is available for these antibodies, the designations for which are the initials of human patients from which they were derived. The structure of antibody HIL is also known now (Brookhaven Code P8FAB).

Once the sequences are thus compared, residue identities are noted and percent identities are determined. All other factors being equal, it is desirable to select a human antibody which has the highest percent identity with the animal antibody.

(2) Sequence Ambiguities

The known human antibody chain sequences are then evaluated for the presence of unidentified residues and/or ambiguities, which are sequence uncertainties. The most common of such uncertainties are mistaken identification of an acidic amino acid for an amide amino acid due to loss of ammonia during the sequencing procedure, e.g., incorrect identification of a glutamic acid residue, when the residue actually present in the protein was a glutamine residue. Uncertainties are identified by examination of data bases such as that of Kabat et al., supra. All other factors being equal, it is desirable to select a human antibody chain having as few such ambiguities as possible.

(3) Pin-region Spacing

Antibody chain variable regions contain intra-domain disulfide bridges. The distance (number of residues) between the cysteine residues comprising these bridges is referred to as the Pin-region spacing [Chothia et al., *J. Mol. Biol.* 196:901 (1987)]. All other factors being equal, it is most desirable that the Pin-region spacing of a human antibody selected be similar or identical to that of the animal antibody. It is also desirable that the human sequence Pin-region spacing be similar to that of a known antibody 3-dimensional structure, to facilitate computer modeling.

Based upon the foregoing criteria, the human antibody (or antibodies) having the best overall combination of desirable characteristics is selected as the framework for humanization of the animal antibody. The heavy and light chains selected may be from the same or different human antibodies.

The second step in the methods of this invention involves determination of which of the animal antibody variable region sequences should be selected for grafting into the human framework. This selection process is based upon the following selection criteria:

(1) Residue Selection

Two types of potential variable region residues are evaluated in the animal antibody sequences, the first of which are called "minimal residues." These minimal residues comprise CDR structural loops plus any additional residues required, as shown by computer modeling, to support and/or orient the CDR structural loops.

The other type of potential variable region residues are referred to as "maximal residues." They comprise the minimal residues plus Kabat CDRs plus any additional residues which, as determined by computer modeling, fall within about 10 Å of CDR structural loop residues and possess a water solvent accessible surface [Lee et al., *J. Biol. Chem.* 55:379 (1971)] of about 5 Å$^2$ or greater. In the Example below, residues falling within 5 Å of CDR structural loops were selected.

(2) Computer Modeling

To identify potential variable region residues, computer modeling is carried out on (a) the variable region sequences of the animal antibody that is to be humanized, (b) the selected human antibody framework sequences, and (c) all possible recombinant antibodies comprising the human antibody framework sequences into which the various minimal and maximal animal antibody residues have been grafted.

The computer modeling is performed using software suitable for protein modeling and structural information obtained from an antibody that (a) has variable region amino acid sequences most nearly identical to those of the animal antibody and (b) has a known 3-dimensional structure. An example of software that can be used is the SYBYL Biopolymer Module software (Tripos Associates). The antibody from which the structural information can be obtained may be but need not necessarily be a human antibody. For the Example below, structural information from a murine antibody designated 1F19 was used.

Based upon results obtained in the foregoing analysis, recombinant chains containing the animal variable regions producing a computer modeling structure most nearly approximating that of the animal antibody are selected for humanization.

The nucleotide sequences of cDNAs encoding the partial heavy and complete light chain variable regions of anti-human IL-5 monoclonal antibody JES1-39D10, the production of which is described below, are defined in the Sequence Listing by SEQ ID NOs: 1 and 2, respectively. The amino acid sequences predicted from these nucleotide sequences are also defined in SEQ ID NOs: 1 and 2.

In the nucleotide sequence defined by SEQ ID NO: 1 (heavy chain sequence), bases 1 to 26 were derived from a polymerase chain reaction (PCR) primer. Therefore, the cloned sequence begins at base. 27. The corresponding amino acid sequence from SEQ ID NO: 1 is that of the mature polypeptide of $V_H$, not including the leader or the first fourteen residues of framework 1. In the nucleotide sequence defined by SEQ ID NO: 2 (light chain sequence), bases 1 and 2 were derived from a PCR primer. Therefore, the cloned sequence begins at base 3. The corresponding amino acid sequence is that of the leader and the mature polypeptide of $V_L$.

The CDRs of the heavy chain variable region of monoclonal antibody JES1-39D10 as determined by the method of Kabat et al., supra, comprise amino acid residues 26–30, 45–60 and 93–100 of the amino acid sequence defined by SEQ ID NO: 1. As determined by computer analysis of binding site loop structures as described below, the CDR structural loops of the heavy chain variable region of monoclonal antibody JES1-39D10 comprise amino acid residues 21–27, 47–50 and 93–101 of the amino acid sequence defined by SEQ ID NO: 1.

Nucleotide sequences encoding the foregoing heavy chain CDRs comprise bases 76–90, 133–180 and 277–300 (Kabat determination) and bases 61–81, 139–150 and 277–303 (loop analysis) of the nucleotide sequence defined by SEQ ID NO: 1.

The CDRs of the light chain variable region of monoclonal antibody JES1-39D10 as determined by the method of Kabat et al., supra, comprise amino acid residues 44–54, 70–76 and 109–117 of the amino acid sequence defined by SEQ ID NO: 2. As determined by computer analysis of binding site loop structures as described below, the CDR structural loops of the light chain variable region of monoclonal antibody JES1-39D10 comprise amino acid residues 46–51, 70–72 and 111–116 of the amino acid sequence defined by SEQ ID NO: 2.

Nucleotide sequences encoding the foregoing light chain CDRs comprise bases 130–162, 208–228 and 325–351 (Kabat determination) and bases 136–222, 208–216 and 331–348 (loop analysis) of the nucleotide sequence defined by SEQ ID NO: 2.

From the foregoing, it can be seen that the CDRs thus determined are encoded by from 9 to 48 bases. Useful DNAs for protein engineering therefore comprise from about 12 to 333 bases and from about 9 to 384 bases of the nucleotide sequences defined by SEQ ID NOs: 1 and 2, respectively. Also of importance is the constant region for selection of isotype for protein engineering.

If the CDRs of the invention are used to produce humanized antibodies by grafting onto a human antibody, it may be desirable to include one or more amino acid residues which, while outside the CDRs, are likely to interact with the CDRs or IL-5 (Queen et al., supra).

The CDRs of the invention can also form the basis for the design of non-peptide mimetic compounds which mimic the functional properties of antibody JES1-39D10. Methods for producing such mimetic compounds have been described by Saragovi et al. [*Science* 253:792 (1991)].

In addition to providing a basis for antibody humanization, the information in SEQ ID NOs: 1 and 2 can be used to produce single-chain IL-5 binding proteins comprising linked CDRs from the light and/or heavy chain variable regions, as described by Bird et al. [*Science* 242:423 (1988)], or biosynthetic antibody binding sites (BABS), as described by Huston et al. [*Proc. Natl. Acad. Sci. USA* 85:5879 (1988)]. Single-domain antibodies comprising isolated heavy-chain variable domains [Ward et al., *Nature* 341:544 (1989)] can also be prepared using the information in SEQ ID NO: 1.

Two or more CDRs of the invention can also be coupled together in a polypeptide, either directly or by a linker sequence. One or more of the CDRs can also be engineered into another (non-immunoglobulin) polypeptide or protein, thereby conferring IL-5 binding capability on the polypeptide or protein.

Polypeptides "comprising a heavy or light chain variable region of a monoclonal antibody having a sequence defined by SEQ ID NOs: 1 or 2, or a subsequence thereof", are defined herein to include all of the foregoing CDR-containing embodiments.

DNAs which encode the heavy and light chain variable regions of antibody JES1-39D10 or the CDRs therefrom can be prepared by standard methods using the nucleic acid sequence information provided in SEQ ID NOs: 1 and 2. For example, such DNA can be chemically synthesized using, e.g., the phosphoramidite solid support method of Matteucci et al. [*J. Am. Chem. Soc.* 103:3185 (1981)], the method of Yoo et al. [*J. Biol. Chem.* 764:17078 (1989)], or other well known methods.

Alternatively, since the sequence of the gene and the site specificities of the many available restriction endonucleases are known, one skilled in the art can readily identify and isolate the gene from the genomic DNA of the hybridoma producing monoclonal antibody JES1-39D10 and cleave the DNA to obtain the desired sequences. The PCR method [Saiki et al., *Science* 239:487 (1988)], as exemplified by Daugherty et al. [*Nucleic Acids Res.* 19:2471 (1991)] can also be used to obtain the same result. Primers used for PCR can if desired be designed to introduce appropriate new restriction sites, to facilitate incorporation into a given vector.

Still another method for obtaining DNAs encoding the heavy and light chain variable regions of antibody JES1-39D10 entails the preparation of cDNA, using mRNA isolated from the hybridoma producing monoclonal antibody JES1-39D10 as a template, and the cloning of the variable regions therefrom using standard methods [see, e.g., Wall et al., *Nucleic Acids Res.* 5:3113 (1978); Zalsut et al., *Nucleic Acids Res.* 8:3591 (1980); Cabilly et al., *Proc. Natl. Acad. Sci. USA* 81:3273 (1984); Boss et al., *Nucleic Acids Res.* 12:3791 (1984); Amster et al., *Nucleic Acids Res.* 8:2055 (1980); Moore et al., U.S. Pat. No. 4,642,234].

Of course, due to the degeneracy of the genetic code, many different nucleotide sequences can encode CDRs, polypeptides and antibodies having amino acid sequences defined by SEQ ID NOs: 1 and 2 and the CDRs therein. Similarly, humanized antibodies having amino acid sequences described below can be encoded by many different DNAs.

The particular codons used can be selected for both convenient construction and optimal expression in prokaryotic or eukaryotic systems. Such functional equivalents are also a part of this invention. Furthermore, those skilled in the art are aware that there can be conservatively modified variants of polypeptides and proteins in which there are minor amino acid substitutions, additions or deletions that do not substantially alter biological function [Anfinsen, *Science* 181:223 (1973); Grantham, *Science* 185:862 (1974)].

Such conservatively modified variants of the amino acid sequences defined by SEQ ID NOs: 1 and 2 and of the humanized antibodies described below are also contemplated by this invention. It is well within the skill of the art, e.g., by chemical synthesis or by the use of modified PCR primers or site-directed mutagenesis, to modify the DNAs of this invention to make such variants if desired.

It may also be advantageous to make more substantial modifications. For example, Roberts et al. [*Nature* 328:731 (1987)] have produced an antibody with enhanced affinity and specificity by removing two charged residues at the periphery of the combining site by site-directed mutagenesis.

Insertion of the DNAs encoding the heavy and light chain variable regions of antibody JES1-39D10 into a vector is easily accomplished when the termini of both the DNAs and the vector comprise compatible restriction sites. If this cannot be done, it may be necessary to modify the termini of the DNAs and/or vector by digesting back single-stranded DNA overhangs generated by restriction endonuclease cleavage to produce blunt ends, or to achieve the same result by filling in the single-stranded termini with an appropriate DNA polymerase. Alternatively, any site desired may be produced by ligating nucleotide sequences (linkers) onto the termini. Such linkers may comprise specific oligonucleotide sequences that define desired restriction sites. The cleaved vector and the DNA fragments may also be modified if required by homopolymeric tailing or PCR.

Pharmaceutical compositions can be prepared using the antibodies, binding compositions or single-chain binding proteins of the invention, or anti-idiotypic antibodies prepared against such monoclonal antibodies, to treat IL-5-related diseases. Fragments of the antibodies such as Fab or Fv fragments, isolated heavy or light chains or fragments therefrom, and short polypeptides comprising, e.g., individual CDR regions, can also be used in such compositions.

Some of the compositions have IL-5 blocking or antagonistic effects and can be used to suppress IL-5 activity. Such compositions comprise the antibodies, binding compositions or single-chain binding proteins of the invention and a physiologically acceptable carrier.

Other compositions comprise anti-idiotypic antibodies prepared using the monoclonal antibodies of the invention as an antigen and a physiologically acceptable carrier. These anti-idiotypic antibodies, which can be either monoclonal or polyclonal and are made by standard methods, may mimic the binding activity of IL-5 itself. Thus, they may potentially be useful as IL-5 agonists or antagonists.

Useful pharmaceutical carriers can be any compatible, non-toxic substance suitable for delivering the compositions of the invention to a patient. Sterile water, alcohol, fats, waxes, and inert solids may be included in a carrier. Pharmaceutically acceptable adjuvants (buffering agents, dispersing agents) may also be incorporated into the pharmaceutical composition. Generally, compositions useful for parenteral administration of such drugs are well known; e.g. *Remington's Pharmaceutical Science*, 15th Ed. (Mack Publishing Company, Easton, Pa., 1980). Alternatively, compositions of the invention may be introduced into a patient's body by implantable drug delivery systems [Urquhart et al., *Ann. Rev. Pharmacol. Toxicol.* 24:199 (1984)].

EXAMPLE

In the following non-limiting Example used for the purpose of illustration, percentages for solids in solid mixtures, liquids in liquids, and solids in liquids are given on a wt/wt, vol/vol and wt/vol basis, respectively, unless otherwise indicated. Sterile conditions were maintained during cell culture.

General Methods and Reagents

Unless otherwise noted, standard recombinant DNA methods were carried out essentially as described by Maniatis et al., Molecular Cloning: A Laboratory Manual, 1982, Cold Spring Harbor Laboratory.

Small scale isolation of plasmid DNA from saturated overnight cultures was carried out according to the procedure of Birnboim et al. [*Nucleic Acids Res.* 7:1513 (1979)]. This procedure allows the isolation of a small quantity of DNA from a bacterial culture for analytical purposes. Unless otherwise indicated, larger quantities of plasmid DNA were prepared as described by Clewell et al. [*J. Bacteriol.* 110:1135 (1972)].

Specific restriction enzyme fragments derived by the cleavage of plasmid DNA were isolated by preparative electrophoresis in agarose. Gels measuring 9×5½ cm were run at 50 mA for 1 hour in Tris-Borate buffer (Maniatis et al., supra, p. 454) and then stained with 0.5 $\mu$g/ml ethidium bromide to visualize the DNA. Appropriate gel sections were excised, and the DNA was electroeluted (Maniatis et al., supra, p. 164). After electroelution, the DNA was phenol extracted (Maniatis et al., supra, p. 458) and ethanol precipitated at −20° C. (Maniatis et al., supra, p. 461).

Restriction enzymes and T4 DNA ligase were purchased from New England Biolabs (Beverly, Mass.). Superscript RNAse H- reverse transcriptase was from BRL/GIBCO (Gaithersburg, Md.), Taq DNA polymerase from Stratagene (LaJolla, Calif.), DNA polymerase Klenow fragment from Pharmacia LKB Biotechnology, Inc. (Piscataway, N.J.), calf intestinal phosphatase from Boehringer Mannheim Biochemicals (Indianapolis, Ind.) and RNAsin from Promega (Madison, Wis.). All enzymes were used in accordance with the manufacturers' instructions. The Sequenase version 2.0 sequencing system was obtained from United States Biochemical (Cleveland, Ohio).

Deoxynucleotide triphosphates and oligo $dT_{12-18}$ primer were from Pharmacia LKB Biotechnology, bovine serum albumin (BSA) from Boehringer Mannheim Biochemicals and re-distilled phenol from BRL/GIBCO.

Plasmid vectors pSV.Sport and pUC19, and competent *E. Coli* strain DH5-alpha (Max Efficiency) were from BRL/GIBCO. COS-7 cells (ATCC CRL 1651) were obtained from the American Type Culture Collection, Bethesda, Md. Tissue culture media, fetal bovine serum (FBS) and supplements were from BRL/GIBCO.

Recombinant human IL-5 was expressed in Chinese hamster ovary (CHO) cells by standard methods using plasmid pDSRG (ATCC 68233) and purified by immunoaffinity chromatography.

Rabbit antiserum against recombinant human IL-5 was made by standard methods. Biotinylated goat anti-rabbit IgG was obtained from Vector Labs, Burlingame, Calif., while streptavidin-alkaline phosphatase conjugate was a product of BRL/GIBCO. Biotinylated rabbit anti-rat IgG was from Jackson Labs, West Grove, Pa. Nitro blue tetrazolium (NBT) and 5-bromo-4-chloro-3-indolyl phosphate (BCIP) were obtained from BRL/GIBCO.

A highly sensitive ELISA AMPLIFICATION SYSTEM® used as the substrate for microtiter plate ELISA (enzyme-linked immunosorbent assay) determinations was obtained from BRL/GIBCO.

Cell Culture

The hybridoma cell line producing monoclonal antibody JES1-39D10 was produced as described by Denburg et al. [*Blood* 77:1462 (1991)] and initially maintained in Dulbecco's Modified Eagle's medium (DMEM/high glucose; GIBCO, Bethesda, Md.) supplemented with 5% FBS, 2 mM glutamine and 10 units/ml penicillin/streptomycin in a humidified 37° C. chamber with 5% $CO_2$. Subsequently, the cell line was adapted to serum-free culture by replacing the serum with 1X HB101 supplement (Hana Biologics, Alameda, Calif.).

Characterization of Monoclonal Antibody JES1-39D10 Purification

Medium conditioned by the cell line producing antibody 39D10.11 (a subclone of JES1-39D10) was harvested, filtered and applied to an antigen affinity column prepared by coupling recombinant human IL-5 to AFFIGEL-15® resin (BioRad, Richmond, Calif.). The column was then washed sequentially with phosphate buffered saline (PBS) and PBS with 0.5 M NaCl, and then equilibrated with PBS. Antibody 39D10.11 was eluted from the column with 0.2 M glycine buffer, pH 2.95, after which the eluted protein was neutralized immediately with 1 M Tris-HCl, pH 8.

The purified protein was subjected to polyacrylamide gel electrophoresis (SDS-PAGE) in a 15% gel under reducing conditions essentially as described by Laemmli [*Nature* 227:680 (1970)], to separate the heavy and light chains. Both chains were recovered by transfer onto an IMMO-BILON® membrane (a PVDF membrane from Millipore, Bedford, Mass.), essentially using the electroblotting method of Matsudaira [*J. Biol. Chem.* 261:10035 (1987)].

Bands corresponding to the heavy and light chains were excised from the membrane following staining with Coomassie Brilliant Blue and processed for N-terminal sequencing using an Applied Biosystems Model 477A protein-peptide sequencer. Sequencing of the isolated heavy and light chains blotted onto the IMMOBILON® membrane was carried out essentially as described by Yuen et al. [*Biotechniques* 7:74 (1989)].

The heavy chain could not be sequenced under standard conditions. The light chain was sequenced up to 15 cycles. Comparison of the sequence obtained with published data confirmed the identity of a rat immunoglobulin light chain.

Antibody Isotyping

Isotyping of antibody JES1-39D10 carried out using a kit from Zymed (San Francisco, Calif.) revealed that heavy chain was a gamma 2a isotype and the light chain was a kappa isotype (γ2a/κ isotype).

Effect on Biological Activity

Monoclonal antibody JES1-39D10 strongly inhibits the biological activity of recombinant human IL-5 (Denburg et al., supra). Studies have shown that the antibody-produces this effect by inhibiting the binding of the IL-5 to its cellular receptors.

PCR Cloning

Oligonucleotide Primer Design and Cloning Strategy

Briefly, oligonucleotide primers were prepared corresponding to the known amino- and carboxyl-termini of rat IgG2a and kappa heavy and light chain sequences [Reichmann et al., *Nature* 332:323 (1988); Bruggemann et al., *Proc. Natl. Acad. Sci. USA* 83:6075 (1986); Hellman et al., *Gene* 40:107 (1985)]. Using these primers, cDNA fragments of the complete light chain and a truncated heavy chain were isolated using the PCR method [Saiki et al., *Science* 239:487 (1988)]. The cDNA fragments were sequenced and confirmed by comparison with other clones generated using PCR primers designed from different regions of the cDNAs. The deduced amino acid sequence of the light chain was verified by the sequencing of the first 15 N-terminal amino acid residues of the JES1-39D10 light chain.

Oligonucleotide Synthesis

Based upon the IgG2a/kappa isotype of antibody JES1-39D10, oligonucleotide primers having sequences defined in the Sequence Listing were synthesized by standard methods using an Applied BioSystems Model 380A or 380B Synthesizer.

The designations of these primers (with the first letter corresponding to the synthesizer model used) and the corresponding sequence identification numbers are as follows:

| Oligonucleotide | SEQ ID NO. |
| --- | --- |
| B2051CC | 3 |
| B2031CC | 4 |
| A2064CC | 5 |
| A2065CC | 6 |
| B2137CC | 7 |
| B2108CC | 8 |
| B2101CC | 9 |
| B1852CC | 10 |

For the heavy chain of antibody JES1-39D10, the 5' end primer B2051CC was derived from a segment of a rat IgG2a sequence published by Reichmann et al., supra, encompassing the sixth through the fourteenth amino acid residues of the mature heavy chain polypeptide. Two restriction sites, XbaI and HindIII, were added at the 5' end of the primer to facilitate cloning. The 3' end primer B2031CC was based upon a segment of the published rat IgG2a constant region three sequence (Bruggemann et al., supra). Three restriction sites, SmaI, EcoRI and SalI, were added for cloning purposes.

For the light chain, both the 5' and 3' end primer sequences were derived from a published rat kappa mRNA sequence (Hellman et al., supra). Primer A2064CC encompasses a partial 5' untranslated region and the first two nucleotides of the translation initiation codon. A HindIII and a BamHI site were added to facilitate cloning. The 3' end primer A2065CC was based upon a segment of a published rat kappa immunoglobulin light chain 3' untranslated region (3' UTR). This segment encompasses the last two nucleotides of the stop codon and 22 3' UTR nucleotides immediately 3' of the stop codon. EcoRI and PstI sites were added to facilitate cloning.

PCR Reaction Conditions

Total cytoplasmic RNA was isolated from the hybridoma cell line producing antibody JES1-39D10, essentially as described by Cathala et al. [*DNA* 2:329 (1983)]. First-strand cDNA synthesis was carried out using the isolated RNA as the template, essentially as described by by Larrick et al. [*Bio/Technology* 7:934 (1989)]. The cDNA product was then subjected to PCR in a 50 μl volume reaction mixture with a 50 μl paraffin oil overlay, in a 0.5 ml Eppendorf tube.

The reaction mixture for heavy chain synthesis contained 26.5 μl of $H_2O$, 5 μl of Taq (Thermus aquaticus) DNA polymerase buffer [final concentrations in the reaction: 10 mM Tris-HCl, pH 8.3, 50 mM KCl, 1.5 mM $MgCl_2$, 0.01% (w/v) gelatin], 5 μl of 1.25 mM dNTP, 4 μl of primer B2051CC (60 pmol), 4 μl of primer B2031CC (60 pmol), 5 μl of cDNA (containing half of the first-strand cDNA derived from 3–6 μg total RNA) and 0.5 μl of Taq polymerase (2.5 units). The reaction mixture for light chain synthesis was similar, except that the primers used were A2064CC and A2065CC.

The reaction was carried out in a PHC-1 Thermocycler (Techne, Princeton, N.J.) with 30 cycles of: 94° C., 1.5 minutes for denaturation; 50° C., 2 minutes for annealing;

and 72° C., 3.5 minutes for synthesis. At the end of the 30th cycle, the reaction mixture was incubated another 9 minutes at 72° C. for extension.

The PCR mixture was subjected to electrophoresis in a 1% agarose/Tris-Borate gel containing 0.5 μg/ml ethidium bromide. DNA fragments having the expected sizes (approximately 1.5 kilobases for the heavy chain, approximately 0.7 kilobases for the light) were excised from the gel and purified by electroelution.

Verification of cDNA Clones

DNA Sequencing

Following recovery from the gel, ethanol precipitation and restriction endonuclease cleavage, the PCR-generated putative heavy and light chain cDNAs were cloned into an appropriate vector for sequencing.

The putative heavy and light chain cDNAs were cloned separately into the pUC19 vector as HindIII/EcoRI and BamHI/PstI fragments, respectively. The ligated plasmids were then transformed into *E. coli* strain DH5-alpha using standard methods. Transformant colonies were isolated, and plasmid DNA from at least two clones each for the heavy and light chains was prepared from the transformants for sequencing.

Comparison of the variable region sequences thereby obtained (defined for the heavy and light chains by SEQ ID NOs: 1 and 2, respectively) with the published immunoglobulin sequences revealed a high degree of homology in the framework and in the positioning of the putative CDRs as determined by the method of Kabat et al., supra. Moreover, the N-terminal amino acid sequence predicted from the light chain cDNA sequence agreed with the experimentally-determined N-terminal sequence of the light chain of antibody JES1-39D10.

Expression Plasmid Construction

To confirm that the isolated cDNAs encoded proteins that could specifically bind to human IL-5, cDNA encoding a full-length putative heavy chain of antibody JES1-39D10 was reconstructed by PCR. Primers B2137CC (SEQ ID NO: 7) and B2108CC (SEQ ID NO: 8) were designed to modify the initially-cloned truncated heavy chain cDNA. These primers supplied sequences encoding the leader peptide, five missing amino acid residues at the N-terminus of the variable region, and missing residues at the C-terminus of the constant region.

A vertebrate consensus translational initiator sequence [Kozak, *Nucleic Acids Res.* 20:8125 (1987)] was added to the 5' end of the coding cDNA to facilitate translation. To facilitate cloning, SalI and EcoRI restriction sites were introduced into the 5' and 3' ends, respectively, of the resulting cDNA.

The putative light chain cDNA was also re-engineered, using primers B2101CC (SEQ ID NO: 9) and B1852CC (SEQ ID NO: 10). This was done primarily to modify the restriction sites at the ends for expression plasmid construction. The vertebrate consensus translational initiator sequence was also introduced into this cDNA.

PCR was carried out and the DNA products were isolated as described above, and the DNAs were cleaved with SalI and EcoRI. The heavy and light chain cDNAs were then ligated separately into expression vector pSRS (ATCC 68234) which had been similarly cleaved. Plasmid pSRS contains an SRa promoter and an SV40 origin of replication to enable replication and expression of the cDNA inserts in COS cells.

Transfection

Prior to transfection, COS cells were propagated in DMEM/high glucose supplemented with 10% FBS and 6 mM glutamine. Exponentially grown cells were trypsinized, washed with fresh medium, and then resuspended in fresh medium at a density of $2 \times 10^7$ cells/ml.

Electroporation was carried out using a GENEPULSER® (BioRad, Richmond, Calif.) according to the manufacturer's instructions. Briefly, a 250 μl aliquot of the COS cell suspension was dispensed into each cuvette. About 10 μg of CIRCLEPREP® (Bio101, LaJolla, Calif.)-purified plasmid DNA was added in a volume of less than 50 μl to the cuvettes and was mixed with the cells. DNA samples used included pSRS with the heavy chain cDNA insert (pSRS-H), pSRS with the light chain cDNA insert (pSRS-L), an equal amount mixture of pSRS-H and pSRS-L, and unmodified pSRS.

A 0.2 volt electrical pulse was delivered at 960 μF with a capacity extender. The cells were then plated in 60 mm culture dishes, fed with 5 ml of fresh medium and incubated at 37° C. in a 5% $CO_2$ incubator. After 16 hours, the medium was removed by aspiration and replaced with serum-free medium. Incubation was continued for an additional 72 hours, after which the medium was harvested.

Immunoblot Analysis

The serum-free media conditioned by the transfected cells were concentrated about ten fold by centrifugation in CENTRICON® tubes (Amicon, Danvers, Mass.), after which they were subjected to electrophoresis in a 15% precast SDS polyacrylamide, gel (Integrated Separation Systems, Hyde Park, Mass.) under non-reducing conditions. Two identical sets of samples were applied to the same gel. Two identical molecular weight marker protein mixtures (containing 97.4, 68, 43, 29, 18.4 and 14.3 kilodalton proteins) were also run in the gel.

Following electrophoresis, the separated bands were transferred onto a nitrocellulose membrane using a Semi-dry Electroblotter (Integrated Separation Systems, Hyde Park, Mass.). The membrane was then incubated at room temperature with 3% BSA in PBS, after which the membrane was cut into two pieces. Each piece contained a complete set of the samples.

One piece of the membrane was used in a first analysis to detect rat IgG chain expression in the conditioned media. This was accomplished by treating the membrane in turn at room temperature: once with a 1:200 dilution of biotinylated rabbit anti-rat IgG in TBST buffer [10 mM Tris-HCl, pH 7.4, 150 mM NaCl and 0.05% TWEEN-20® (polyoxyethylenesorbitan monolaurate)] with 3% BSA for 45 minutes, three times with TBST buffer alone for 15 minutes, once with a 1:10,000 dilution of streptavidin-alkaline phosphatase conjugate in TBST buffer for 30 minutes, three times with TBST buffer alone for 15 minutes, and once with alkaline phosphatase substrate (44 μl of NBT and 33 μl of BCIP in 10 ml of an alkaline phosphatase buffer containing 100 mM Tris-HCl, pH 9, 100 mM NaCl, 5 mM $MgCl_2$) for 10–30 minutes. The membrane piece was then examined for color development after rinsing with distilled water.

The other piece of the membrane was used in a second analysis to determine whether a human IL-5 binding protein was present in any of the conditioned media. This piece was treated sequentially at room temperature: once with 1 μg/ml recombinant human IL-5 in TBST buffer for 1 hour, three times with TBST buffer alone for 15 minutes, once with a 1:3,000 dilution of a rabbit antiserum against recombinant human IL-5 in TBST buffer for 1 hour, three times with TBST buffer alone for 15 minutes, once with a 1:200 dilution of biotinylated goat anti-rabbit IgG in TBST buffer for 1 hour, three times with TBST buffer alone for 15 minutes, once with a 1:10,000 dilution of streptavidin-alkaline phosphatase conjugate in TBST buffer for 30 minutes, three times with TBST buffer alone for 15 minutes, and once with the alkaline phosphatase substrate for 30 minutes. The membrane piece was then examined for color development.

The results of the first analysis showed that only the medium conditioned by the transformant cotransfected with both plasmids pSRS-H and pSRS-L produced detectable bands. The pattern of bands was as expected for immunoglobulins. Staining was not observed in the lanes containing conditioned media from cells transfected with heavy or light chain alone, indicating either low quantities of protein or an inability of the antibody to recognize individual heavy and light chains. Heavy chain was not expected to be present in the conditioned media, since it is usually not secreted in the absence of a light chain [Bole et al., *J. Cell Biol.* 102:1558 (1986)].

In the second analysis, strong IL-5 binding activity was observed in the sample from the medium conditioned by the transformant cotransfected with both plasmids pSRS-H and pSRS-L. This was noted as a major stained band in a nonreducing SDS gel migrating with an apparent molecular weight of about 160 kilodaltons, a size expected for a complete antibody molecule.

Enzyme-Linked Immunosorbent Assay

To confirm the ability of the recombinant monoclonal antibody to specifically bind to human IL-5, a 96-well immunoassay (EIA) plate was coated with 50 μl aliquots of 3% BSA alone, or recombinant human IL-5 (5 μg/ml, followed by blocking with the BSA solution). All coating was done for approximately 2 hours at 4° C. Aliquots (50 μl) of media conditioned by the various COS cell transformants described above or by the hybridoma cell line producing antibody JES1-39D10 were then added to the wells, and the plate was incubated for 2 hours at 4° C.

Following the incubation, the media in the wells were replaced sequentially using 300 μl aliquots at room temperature: three times with TBST buffer alone for 15 minutes, once with biotinylated rabbit anti-rat IgG for approximately 2 hours, three times with TBST alone for 15 minutes, once with streptavidin-alkaline phosphatase conjugate in TBST buffer for 30 minutes, three times with TBST buffer alone for 15 minutes, and then developed with the BRL ELISA AMPLIFICATION SYSTEM® for 5–15 minutes, all reagent dilutions being as described above.

The results of this assay showed that both the natural JES1-39D10 antibody (from the medium conditioned by the hybridoma) and the recombinant antibody (from the medium conditioned by the transformant cotransfected with both plasmids pSRS-H and pSRS-L) were retained in wells coated with IL-5, as evidenced by a strong color development. No significant color development above that of background controls (containing no antibody protein) was observed when IL-5 was absent, or when the test samples were conditioned media of cells transfected with vectors encoding heavy or light chains alone.

Antibody Humanization

Homology Modeling

Using the methods described above, it was determined that antibodies HIL and LAY were optimal human framework candidates. HIL or LAY heavy and light chain pairs and combinations thereof were first pursued.

A listing of potential minimal and maximal JES1-39D10 residues that could be grafted into the framework sequences were determined by the above-described methods to be as shown in the following Table.

| | Residues[a] |
|---|---|
| $V_H$ Minimal List: | 21–27, 47–50, 66, 93–101 |
| $V_H$ Maximal List[b]: | 19, 28, 29, 30, 32, 40, 45, 46, 51, 52–60, 71, 89, 92 |
| $V_L$ Minimal List: | 46–51, 68, 70–72, 84, 91, 109, 110–116 |
| $V_L$ Maximal List[b]: | 44, 45, 52–54, 56, 66, 73–76, 88, 89, 117 |

Specific constructs described below contained the following residues from the foregoing Table:

| Humanized Antibody | Residues |
|---|---|
| CMX5-1 | $V_H$ HIL Maximal; $V_L$ LAY Maximal |
| CMX5-2 | $V_H$ HIL Maximal; $V_L$ LAY Maximal (less structural CDR loop H-1 N-terminus) |
| CMX5-3 | $V_H$ LAY Maximal; $V_L$ LAY Maximal |
| CMX5-4 | $V_H$ HIL Minimal; $V_L$ LAY Minimal |
| CMX5-5 | $V_H$ HIL Kabat; $V_L$ LAY Kabat CDRs only CDRs only |

Since the intended use of the humanized antibodies was the neutralization of the biological activity of soluble human IL-5, γ4 was chosen as the constant region for the humanized antibodies. This is because γ4 is the least potent of the four human immunoglobulin isotypes in triggering complement fixation. The human counterpart of the rat κ isotype was chosen for the constant region of the humanized light chains.

Construction of Humanized Antibody CMX5-1

Synthetic CMX5-1 DNA was constructed using a combination of PCR and conventional cloning techniques. The V region was divided into three segments, each of which was designed to contain designated restriction sites at the 5' and 3' ends. Codons were chosen which occur with relatively high frequency in mammalian genes. Palindromic and repeat sequences were avoided or replaced by silent changes in the design of oligonucleotides, to minimize formation of unanticipated secondary structures that may cause sequence rearrangements or deletions.

Oligonucleotides corresponding to the entire heavy chain variable region (VH) of CMX5-1 were synthesized by standard methods.

The designations of these oligonucleotides and the corresponding SEQ ID NOs defining their sequences are as follows:

| Oligonucleotide | SEQ ID NO. |
|---|---|
| B2474CC | 11 |
| B2419CC | 12 |
| B2420CC | 13 |
| B2475CC | 14 |
| B2477CC | 15 |
| B2479CC | 16 |

Pairs of oligonucleotides B2474CC and B2419CC, B2420CC and B2475CC, B2477CC and B2479CC were heat-denatured, annealed, and incubated with Taq polymerase or Pfu (Stratagene, La Jolla, Calif.). In the polymerase chain reactions (PCRs), the two oligonucleotides in each pair were complementary to each other by about 24 to 30 nucleotides. Therefore, each oligonucleotide served as the template for the other.

The PCRs were carried out for 18 cycles, after which the three resulting DNA fragments, corresponding to the three consecutive segments of VH, designated VH1, VH2 and VH3, were electrophoresed in an agarose gel and purified by electroelution.

The relative order of the three VH DNA fragments, restriction sites for cloning, and the multicloning-site map of cloning vector pSV.Sport were as follows:

| Fragment | Restriction Sites | PCR Primers |
| --- | --- | --- |
| $V_H1$ | EcoRI_SpeI | B2474CC + B2419CC |
| $V_H2$ | SpeI_XbaI | B2420CC + B2475CC |
| $V_H3$ | EcoRI/XbaI_SalI/ApaI/SstI | B2477CC + B2479CC |

Multi-cloning Sites of pSV.Sport

PstI/KpnI/RsrII/EcoRI/SmaI/SalI/SpeI/SpeI/NotI/
XbaI/BamHI/HindIII/SnaBI/MluI

Fragment VH1 was restricted with enzymes EcoRI and SpeI and cloned into vector pSV.Sport. Fragment VH2 was subsequently joined to VH 1 in pSV.Sport by directional insertion at SpeI and XbaI sites. Fragment VH3 was separately cloned into pSV.Sport as an EcoRI/XbaI-SalI/ApaI/SstI fragment. The three fragments were verified by DNA sequencing.

Full-length CMX5-1 VH cDNA was assembled by first joining VH3 to a genomic DNA of the γ4 H-chain constant region (CH) and then attaching the VH3-CH fragment to the VH1–VH2 fragment, as is described more fully below.

CMX5-1 VL cDNA was assembled in a similar manner, using six synthetic oligonucleotide primers. These oligonucleotides and the corresponding SEQ ID NOs defining their sequences are as follows:

| Oligonucleotide | SEQ ID NO. |
| --- | --- |
| B2425RCC | 17 |
| B2426CC | 18 |
| B2427CC | 19 |
| B2458CC | 20 |
| B2459CC | 21 |
| B2460CC | 22 |

Three fragments, designated VL1, VL2, and VL3, were derived from oligonucleotide pairs B2425RCC and B2426CC, B2427CC and B2458CC, B2459CC and B2460CC, respectively. These DNA fragments, which correspond to the three consecutive segments of VL, were purified by agarose gel electrophoresis and electroelution.

The relative order of the three VL DNA fragments, restriction sites for cloning, and the multicloning-site map of cloning vector pUC19 were as follows:

| Fragment | Restriction Sites | PCR Primers |
| --- | --- | --- |
| $V_L1$ | PstI_BstEII/XbaI | B2425RCC + B2426CC |
| $V_L2$ | PstI/BstEII_BamHI | B2427CC + B2458CC |
| $V_L3$ | BamHI_SalI | B2459CC + B2460CC |

Multi-cloning Sites of pUC19

EcoRI/SacI/KpnI/SmaI/BamHI/XbaI/SalI/PstI/SphI/
HindIII

VL1, VL2 and VL3 were first cloned separately into vector pUC19 as PstI-BstEII/XbaI, PstI/BstEII-BamHI and BamHI-SalI fragments, respectively. The identities of the three fragments were verified by DNA sequencing. VL1 and VL2 were then assembled together in pUC19 by inserting VL2 as a BstEII-BamHI fragment into the vector already containing VL1.

The assembly of full-length VL cDNA was accomplished by first joining VL3 to light-chain constant region (CL) and then joining the VL1–VL2 and VL3-CL fragments, as is described more fully below.

To facilitate synthesis and secretion of the humanized antibodies, a leader peptide was attached to the amino-termini of both the mature H- and L-chain polypeptides. The amino acid and nucleotide sequences of this leader are those of the leader of the anti-CAMPATH-1 antibodies (Reichmann et al., supra). The coding sequence for the leader peptide (Reichmann et al., supra) was incorporated into both fragments VH1 and VL1.

In an effort to construct DNA encoding a full-length antibody H-chain, the VH synthetic cDNA was combined with human γ4 constant-region genomic DNA (ATCC 57413) using ApaI restriction cleavage and ligation. This procedure was initiated by digesting plasmid pSV.Sport containing VH3 with NotI followed by treatment with Klenow DNA polymerase (Boehringer Mannheim) to generate blunt ends. The resulting DNA was ethanol-precipitated, resuspended, and digested with ApaI. This restricted plasmid DNA was ligated with the ApaI/SmaI restriction fragment of the genomic γ4 constant region.

The VH3-CH genomic DNA was then excised as an XbaI/HindIII fragment and inserted into pSV.Sport already containing VH1–VH2, thereby completing assembling of the full-length heavy chain DNA.

In an effort to produce the antibody chains, plasmids containing the H- and L-chain DNAs were co-transfected into COS cells. Secreted immunoglobulin was undetectable, however, following analysis of the conditioned medium by ELISA or Western blotting. As an alternative, a human γ4 constant-region cDNA was designed and constructed to replace the genomic DNA.

Six oligonucleotide PCR-primers were synthesized for this purpose by standard methods. The designations of these oligonucleotides and the corresponding SEQ ID NOs defining their sequences are as follows:

| Oligonucleotide | SEQ ID NO. |
| --- | --- |
| B2491CC | 23 |
| B2498CC | 24 |
| B2499CC | 25 |
| B2597CC | 26 |
| B2598CC | 27 |
| B2656CC | 28 |

Primers B2491CC, B2499CC and B2598CC correspond to the plus strand of γ4 constant region cDNA. Primers B2498CC, B2597CC and B2656CC correspond to the minus strand. Using human γ4 genomic DNA as the template, three consecutive double-stranded DNA fragments encompassing the entire γ4 constant-region coding cDNA were generated by PCR.

The three CH DNA segments, restriction sites for cloning, and primers used were as follows:

| Segment | Restriction Sites | PCR Primers |
|---|---|---|
| CH A. | SalI__EcoRI | B2491CC + B2498CC |
| CH B. | EcoRI__XhoI/SalI | B2499CC + B2500CC |
| CH C. | SalI/XhoI__NotI | B2598CC + B2656CC |

Segment A was cloned into pUC19 as a SalI-EcoRI restriction fragment. Segment C, as a SalI/XhoI-NotI restriction fragment, was cloned into pSV.Sport. Segment B, as an EcoRI-XhoI/SalI fragment, was cloned into pSV.Sport already containing segment C. All three segments were verified by DNA sequencing.

The γ4 cDNA was assembled by excising segment A with PstI and EcoRI, and cloning this fragment into pSV.Sport already containing segments B and C. The restriction map of the human γ4 CH cDNA and its relative position in pSV.Sport multi-cloning sites are as follows:

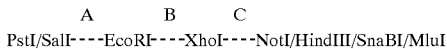

The γ4 CH cDNA was excised as a SalI - - - HindIII fragment to replace the genomic γ4 fragment in the previously described full-length H-chain construct. The final product was a full-length H-chain coding cDNA, cloned in vector pSV.Sport.

Figure 2:
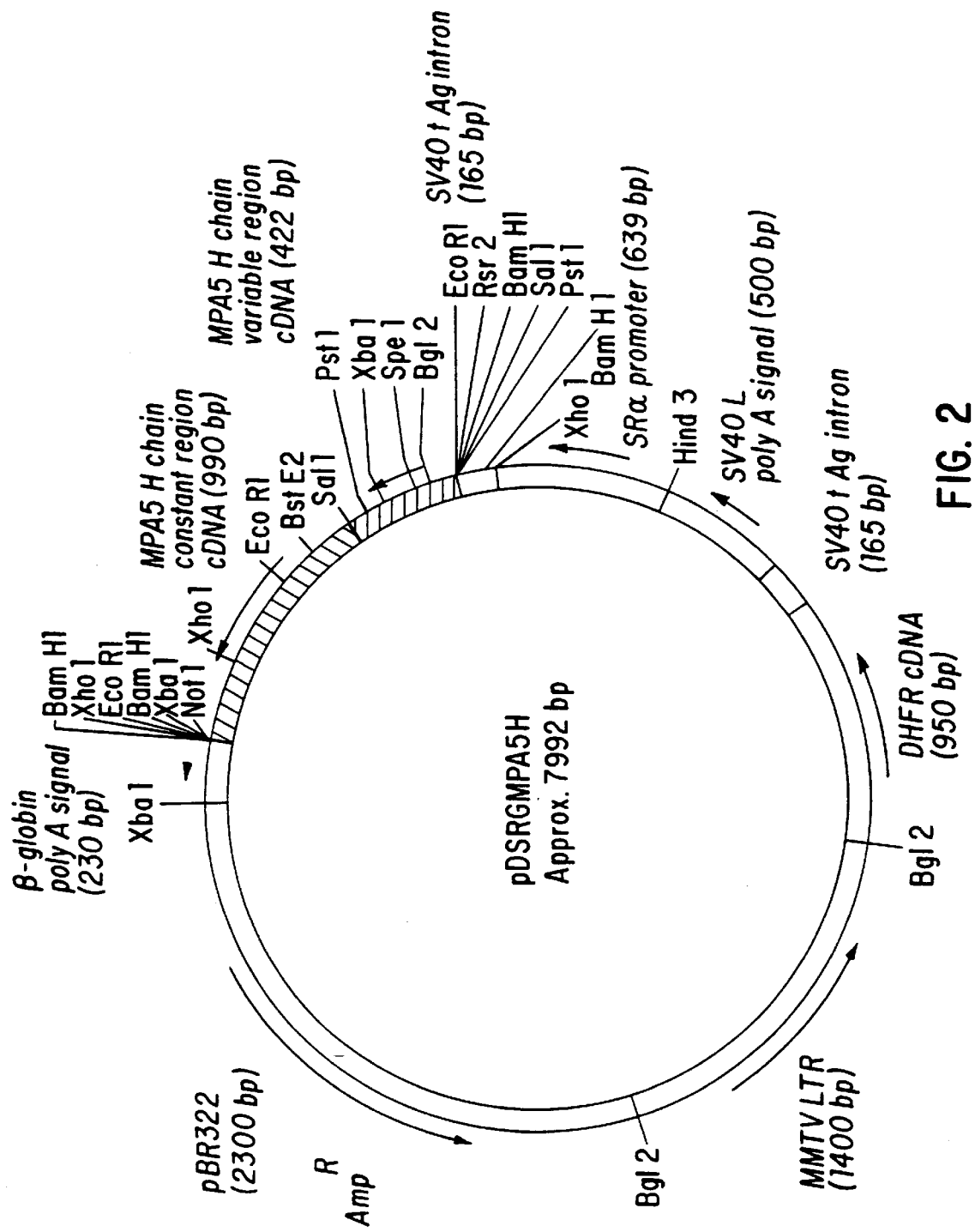
FIG. 2 is a schematic representation of plasmid pDSRGMPA5H.

For stable transfection, plasmid pSV.Sport containing full-length heavy chain cDNA was digested with KpnI and then treated with T4 polymerase to blunt the ends, and then digested with SnaBI. The resulting DNA fragment was isolated by agarose gel electrophoresis followed by purification with a GENECLEAN® DNA purification kit (Bio 101, La Jolla, Calif.), and blunt-end ligated into SmaI-treated plasmid pSRS or pDSRG. The final constructs were designated pSRSMPA5H (FIG. 1) and pDSRGMPA5H (FIG. 2).

The amino terminus of the heavy (H) chain of antibody HIL had previously been reported to be chemically blocked [Chiu et al., *Biochemistry* 18:554 (1977)]. A glutamine codon was assumed as the amino-terminal residue and was used for the H chains of recombinant antibodies CMX1, 2, 4, and 5. In the H chain of antibody CMX5-3, the N-terminal alanine of the LAY H chain was replaced by a glutamic acid residue following comparisons of the LAY H chain amino-terminal residue with corresponding residues of other human H chain sequences in subgroup III, of which the LAY H chain is a member.

To facilitate construction of full-length variant L-chain cDNAs, the codon of glutamic acid residue 105 was replaced by an aspartic-acid codon to create a SalI restriction site near the junction of V$_L$ and C$_L$. This modification enabled substitution of V$_L$ variants as cassettes in the pSV.Sport-based CMX5-1 L-chain expression plasmid.

A human kappa light-chain cDNA was initially constructed based on sequence information from human antibody REI [Epp et al., *Eur. J. Biochem.* 45:513 (1974)]. Seven synthetic oligonucleotide primers were prepared for this purpose, the designations and corresponding SEQ ID NOs of which were as follows:

| Oligonucleotide | SEQ ID NO. |
|---|---|
| B2262CC | 29 |
| B2281CC | 30 |
| B2293CC | 31 |
| B2294CC | 32 |
| A2495CC | 33 |
| A2496CC | 34 |
| B2704CC | 35 |

Four of the oligonucleotide primers were synthesized to encompass a full-length kappa light chain cDNA. These oligonucleotides (B2262CC, B2281CC, B2293CC and B2294CC) were mixed and extended in a single polymerase chain reaction. After the PCR, the product was purified by agarose electrophoresis and electroelution, cloned into pUC19, and analyzed by DNA sequencing. All sequenced clones contained misincorporated bases.

PCR primers A2495CC and A2496CC were then synthesized to generate a correct human κ L-chain constant region. The sequence of A2495CC encompassed the last four amino acid codons of the human LAY antibody V$_L$ framework, and the beginning of the human κ constant region. Primer A2496CC corresponded to the carboxyl terminus of the human κ constant region.

PCR was carried out using an aberrant full-length L-chain clone and primers A2495CC and A2496CC, and the PCR product was cloned into vector pSV.Sport. Sequencing analysis showed, however, that the construct again contained misincorporated bases. This new error was corrected by an additional PCR using oligonucleotide primers A2495CC and B2704CC. The product thereby obtained was cloned as a SalI/HindIII restriction fragment into pUC19 that already carried the V$_L$3 fragment. A correct κ light-chain constant-region cDNA was thus obtained.

Figure 3:
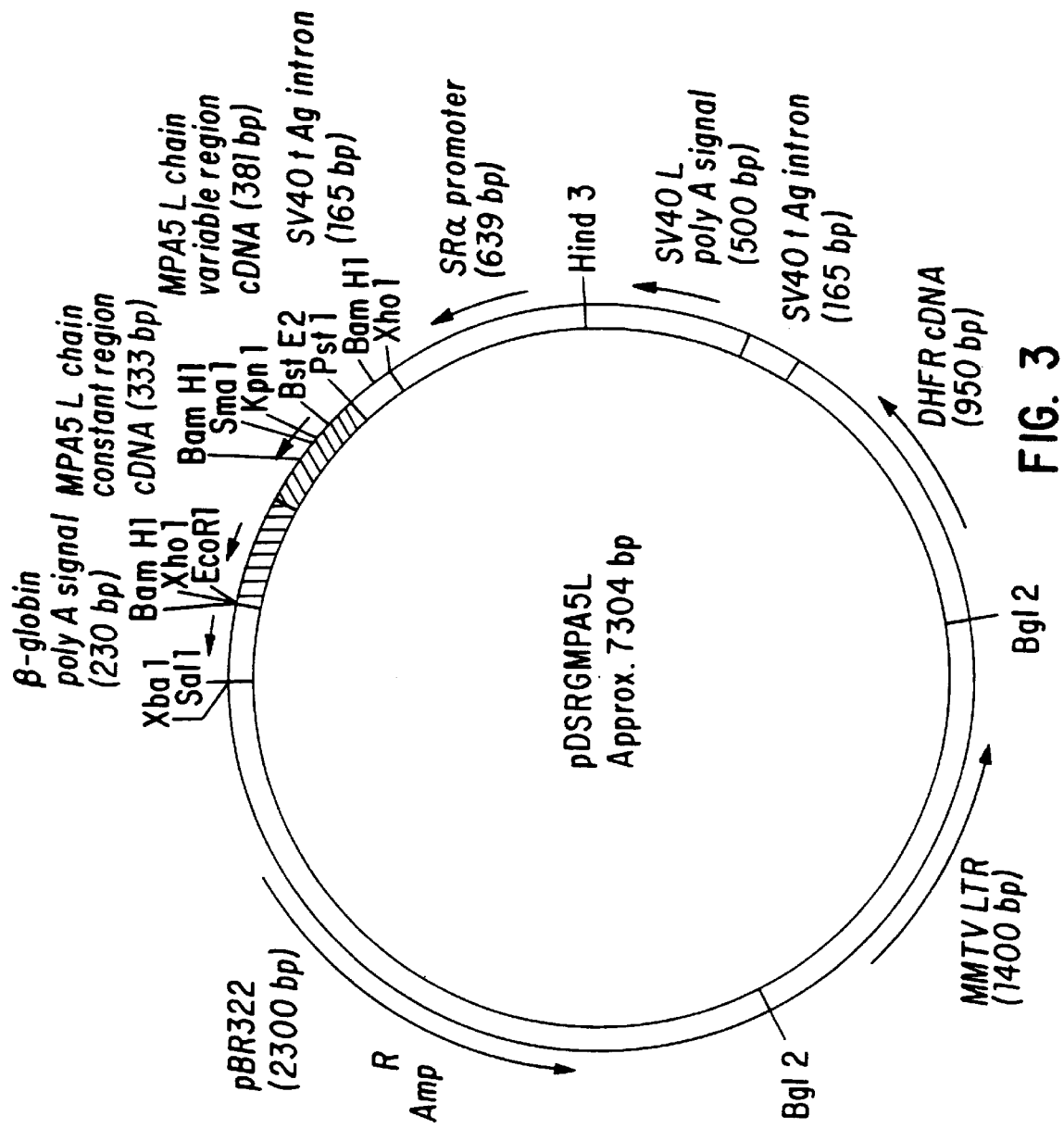
FIG. 3 is a schematic representation of plasmid pDSRGMPA5L.
Figure 4:
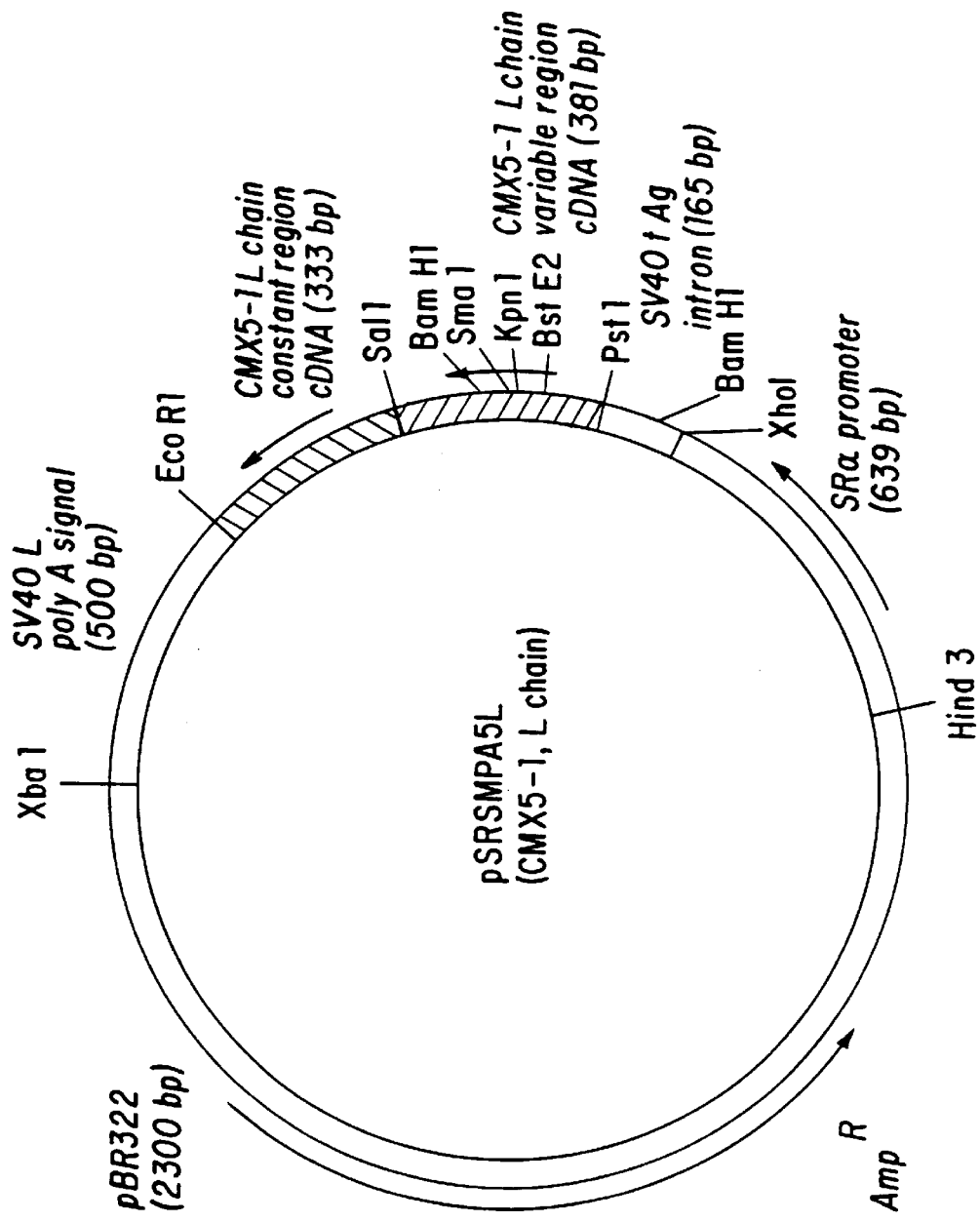
FIG. 4 is a schematic representation of plasmid pSRSMPA5L.

To assemble a full-length L chain cDNA, V$_L$1–V$_L$2 was excised as a blunt-ended HindIII/BamHI fragment and inserted into SmaI/BamHI-cleaved pUC19 containing the V$_L$3-C$_L$ fragment. The full-length light-chain fragment was excised as a PstI/EcoRI fragment from pUC19 and cloned separately into expression vectors pDSRG and pSRS, to generate plasmids designated pDSRGMPA5L (FIG. 3) and pSRSMPA5L (FIG. 4), respectively.

The amino acid sequences of the heavy and light chain variable regions of antibody CMX5-1 are defined in the Sequence Listing by SEQ ID NO: 36 and SEQ ID NO: 37, respectively. Because amino acid residues 1–19 of these sequences comprise a secretory leader that is cleaved during post-translational processing, the actual variable region sequences are defined by the sequences of SEQ ID NO: 36 and SEQ ID NO: 37, beginning with residue 20.

Construction of Humanized Antibody CMX5-2

To construct humanized antibody CMX5-2, complementary oligonucleotides designated B3194CC and B3195CC (sequences defined by SEQ ID NO: 38 and SEQ ID NO: 39, respectively), were synthesized and annealed to form a BglII/SpeI fragment to replace the 42 bp BglII/SpeI fragment of CMX5-1 heavy chain in pSV.Sport. The replaced region was verified by DNA sequencing.

The amino acid sequences of the heavy and light chain variable regions of antibody CMX5-2 are defined in the sequence listing by SEQ ID NO: 40 and SEQ ID NO: 41, respectively. Because amino acid residues 1–19 of these sequences comprise a secretory leader that is cleaved during post-translational processing, the actual variable region sequences are defined by the sequences of SEQ ID NO: 40 and SEQ ID NO: 41, beginning with residue 20.

Construction of Humanized Antibody CMX5-3

To construct CMX5-3 VH, four oligonucleotides were synthesized having amino acid sequences based on antibody JES1-39D10 CDR and human LAY VH framework sequences. The designations and corresponding SEQ ID NOs of these oligonucleotides were as follows:

| Oligonucleotide | SEQ ID NO. |
|---|---|
| B2784CC | 42 |
| B2785CC | 43 |
| B2786CC | 44 |
| B2921CC | 45 |

PCRs were performed using sets of oligonucleotides B2784CC and B2785CC and B2786CC and B2921CC, and the products were restricted to generate a PstI/SpeI fragment and an XbaI/SalI fragment. These DNA fragments were used to replace the VH1 and VH3 fragments, respectively, of the antibody CMX5-1 H chain cDNA in pSV.Sport.

The amino acid sequences of the heavy and light chain variable regions of antibody CMX5-3 are defined in the sequence listing by SEQ ID NO: 46 and SEQ ID NO: 47, respectively. Because amino acid residues 1–19 of these sequences comprise a secretory leader that is cleaved during post-translational processing, the actual variable region sequences are defined by the sequences of SEQ ID NO: 46 and SEQ ID NO: 47, beginning with residue 20.

Construction of Humanized Antibody CMX5-4

Antibody CMX5-4 VH was constructed in a manner analogous to that used to construct antibody CMX5-1. Three sets of overlapping oligonucleotides were synthesized for this purpose, the designations (and defining SEQ ID NOs) of which were as follows:

| Oligonucleotide | SEQ ID NO. |
|---|---|
| B2924CC | 48 |
| B2925CC | 49 |
| B2926CC | 50 |
| B2927CC | 51 |
| B2928CC | 52 |
| B2929CC | 53 |

Using sets of oligonucleotides B2924CC and B2925CC, B2926CC and B2927CC, and B2928CC and B2929CC, three corresponding DNA fragments were synthesized by PCR extension reactions. The three fragments were cloned, sequenced, and assembled in pSV.Sport by restriction digestions and ligations.

CMX5-4 VL was constructed by first annealing oligonucleotides designated B3093XY and B3094XY (sequences defined by SEQ ID NO: 54 and SEQ ID NO: 55, respectively) and then extending the 3' ends of each oligonucleotide by PCR. The product was gel-purified, BstEII and SalI restricted, and used to replace the BstEII/SalI fragment in antibody CMX5-1 L chain cDNA.

The amino acid sequences of the heavy and light chain variable regions of antibody CMX5-4 are defined in the sequence listing by SEQ ID NO: 56 and SEQ ID NO: 57, respectively. Because amino acid residues 1–19 of these sequences comprise a secretory leader that is cleaved during post-translational processing, the actual variable region sequences are defined by the sequences of SEQ ID NO: 56 and SEQ ID NO: 57, beginning with residue 20.

Construction of Humanized Antibody CMX5-5

CMX5-5 VH DNA was constructed by synthesizing two DNA fragments using pairs of oligonucleotides designated B3136CC and B3137CC, and B3138CC and B3202CC, the oligonucleotide sequences of which are defined in the Sequence Listing as follows:

| Oligonucleotide | SEQ ID NO. |
|---|---|
| B3136CC | 58 |
| B3137CC | 59 |
| B3138CC | 60 |
| B3202CC | 61 |

The resulting PCR fragments were gel-purified, restricted, and used to replace the SpeI/BamHI and BamH/SalI fragments in the VH cDNA of antibody CMX5-1.

CMX5-5 VL DNA was constructed by replacing VL3 (a BamHI/SalI fragment) of CMX5-1 in pSRS by a PCR-generated fragment using primers designated B3142CC and B3143CC (sequences defined by SEQ ID NO: 62 and SEQ ID NO: 63, respectively) and template CMX5-1 L.

The amino acid sequences of the heavy and light chain variable regions of antibody CMX5-5 are defined in the Sequence Listing by SEQ ID NO: 64 and SEQ ID NO: 65, respectively. Because amino acid residues 1–19 of these sequences comprise a secretory leader that is cleaved during post-translational processing, the actual variable region sequences are defined by the sequences of SEQ ID NO: 64 and SEQ ID NO: 65, beginning with residue 20.

Antibody Expression and Purification

To express the humanized antibodies, 5–10 µg each of pSRS-based L-chain plasmids and pSV.Sport-based H-chain plasmids were co-transfected into $5 \times 10^6$ COS cells by electroporation protocols. The cells were then plated in a 60 mm culture dish in the presence of complete medium.

After the cells settled and attached to the plates (about 6 hours after transfection and plating), the medium was aspirated and replaced with serum-free medium. Conditioned media were harvested at 72 hours.

The concentrations of humanized antibodies in conditioned media were determined using a human IgG4-specific enzyme-linked immunosorbent assay (ELISA). Nunc Immunoplates were coated at 4° C. for 24 hours with a mouse anti-human IgG4-Fc monoclonal antibody (CalBiochem, La Jolla, Calif.) at 5 µg/ml in 50 mM bicarbonate buffer, pH 9.5. The plates were then blocked at room temperature for 90 minutes with BLOTTO (5% non-fat dried milk and 0.05% (v/v) Tween-20 in Dulbecco's modified phosphate buffered saline).

After washing away excess blocking reagent, serially diluted samples in a volume of 100 µl were applied to wells of the plates. The plates were incubated at 37° C. for 2 hours, after which the samples were aspirated and the wells were washed 3 times. One hundred microliters of sheep anti-human IgG (H+L) peroxidase conjugate (The Binding Site, San Diego, Calif.) were added to each well and the plates were incubated at 37° C. for 2 hours. The plates were then washed 3 times, and 100 µl of ABTS peroxidase substrate (Boehringer Mannheim, Indianapolis, Ind.) was added to each well to produce a color reaction. The plates were read spectrophotometrically at 405 nm.

The conditioned media for all five of the humanized antibodies tested positive for human IgG4. Repeated experiments showed that the concentration of IgG4 was similar in the 3-day condition media for antibodies CMX5-l, CMX5-2, and CMX5-5 (about 200 μg per ml). The IgG4 concentration of CMX5-4 conditioned media was usually about 2 to 3 fold higher. IgG4 levels measured in conditioned medium containing antibody CMX5-3, which contains the V$_H$ framework from the LAY antibody instead of the HIL antibody, were consistently about 5–10 fold lower than the levels measured for antibodies CMX5-1, 2 and 5.

To obtain larger quantities of purified humanized antibodies, recombinant CHO cell lines were established that produced antibody CMX5-1. CMX5-1 H- and L-chain plasmids pSRSMPA5H and pDSRGMPA5L were co-transfected at a ratio of 20:1 into CHO cells, and stable transfectants were selected for resistance to hypoxanthine and thymidine starvation.

Of 106 resistant clones analyzed for human IgG4 secretion prior to methotrexate (MTX) treatment, 65 clones tested positive. When the stable clones were subsequently subjected to methotrexate treatment to produce gene amplification, the majority of the clones appeared to be highly resistant to the drug. Although the cells were treated with MTX at 20, 60 and 200 nM levels, only slight cell growth retardation was observed even at the highest MTX concentration.

One of the better producer clones, designated CJA25, was continuously treated with MTX concentrations that were increased stepwise until a final 1 mM concentration was reached. The final antibody expression level at 1 mM MTX was estimated to be about 15 pg/cell/day. The stability of this cell line was monitored by culturing the cells in the absence of MTX for more than two months, during which the expression level remained unchanged.

In a parallel experiment, CHO cells were again co-transfected with pDSRGMPA5H and pSRSMPA5L but at a ratio of 1:20. The transfection efficiency was found 10 to 100-fold lower, even though the conditions were almost identical to those described above. Screening of 40 clones showed that 10 clones were positive for recombinant human IgG4 secretion.

Levels of antibody JES1-39D10 antibody were measured in a similar fashion except that a goat anti-rat IgG Fc monoclonal antibody (Pierce, Rockford, Ill.) was used as the capture reagent and a sheep anti-rat IgG (H+L) peroxidase conjugate (The Binding Site, San Diego, Calif.) was used as the detection reagent.

Antibodies in the conditioned media were purified by standard methods using protein G or protein A/G (Pierce Chemical) affinity chromatography, as described by the manufacturers of the chromatographic materials. The purified antibodies were more than 99% pure as determined by amino acid composition analysis.

Antibodies in serum-free conditioned media from the JES1-39D10 hybridoma and from clone CJA25 were also purified by affinity chromatography using columns containing immobilized human IL-5. These columns were prepared by coupling purified human IL-5 to AFFIGEL-15® resin (BioRad, Richmond, Calif.).

After loading conditioned medium from one of the sources, the column was washed sequentially with phosphate buffered saline (PBS) and PBS plus 0.5 M NaCl, and then re-equilibrated with PBS. Human IL-5-binding antibodies were then eluted from the column with 0.2 M glycine at pH 2.95, after which the eluted protein was immediately neutralized with 1 M Tris-HCl, pH 8.

The concentration of antibodies thus purified was determined by UV absorption at 280 nm, using determined molar extinction coefficients. The purified proteins were concentrated, dialyzed against phosphate buffered saline, pH 7.2, and subjected to sodium dodecylsulfate polyacrylamide gel electrophoresis [SDS-PAGE; Laemmli, *Nature* 227:680 (1970)] in duplicate 10–20% gels under reducing conditions. After the electrophoresis one gel was stained with Coomassie blue to visualize the protein bands. The proteins in gels run in parallel were recovered by IMMOBILONT blotting, for amino-terminal sequence analyses.

Using this one-step purification method, the recovered protein was estimated to be more than 99% pure, as determined by SDS-PAGE. Under reducing conditions, two bands were observed which had apparent molecular weights of 50 and 23.2 kilodaltons, consistent with the known molecular weights of immunoglobulin H and L chains, respectively.

Antibody Characterization

Affinity Constants

To determine whether the humanized antibodies retained the ability to specifically bind to human IL-5, apparent dissociation constants of antibody/antigen complexes were measured. This was done by coating enzyme immunoassay plates with mouse anti-human IgG$_4$-Fc (5 μg per ml, 100 μl per well) in 50 mM bicarbonate buffer, pH 9.5. The plates were then blocked at room temperature for 90 minutes with BLOTTO, washed 3 times, and incubated at 37° C. for 2 hours with one of the humanized antibodies, either purified (100 μl per well with a final concentration of 0.05 μg per ml) or in the form of conditioned medium (100 μl per well).

The recombinant antibody molecules from the conditioned media thereby became immobilized on the plates through interactions between the constant regions and the precoated antibodies so that the variable regions of the test antibodies were oriented in a uniform manner to allow direct and maximal interactions with the antigen.

To provide a standard for comparison, antibody JES1-39D10 was assayed in parallel, using goat anti-rat IgG Fc instead of the murine anti-human IgG$_4$-Fc as the capture antibody.

After the plates were washed 3 times, a dilution series of $^{125}$I-labeled human IL-5 at concentrations between 4,000 pM and 2 pM was applied to the wells in each plate in final volumes of 100 μl. All test wells were run in triplicate. Background binding was determined by using a 1000-fold molar excess of unlablled human IL-5 in control wells. The reactions were allowed to equilibrate at room temperature for 2 hours, at which time the wells were aspirated and washed 5 times with TBST. The wells were then separated and counted in a Pharmacia LKB γ-counter. All nonspecific binding controls were run in duplicate. The values obtained for bound human IL-5 were subjected to Scatchard analysis (using RADLIG software) to obtain dissociation constant (kd) values.

Results from this analysis showed that the kd values obtained for humanized antibodies CMX5-1, 2, 3 and 5 were all in the same approximate range and were close to that of antibody JES1-39D10. The apparent kd of CMX5-4 could not be determined because very little radioactivity was detected and no dose response was observed.

Competitive Binding Assays

To determine whether humanization introduced alterations in the antigen binding region of antibody JES1-39D10, the wild-type antibody was labeled with biotin using an X-NHS-biotin kit (Calbiochem, La Jolla, Calif.) with a final 20 mM reagent concentration. The product was assayed in a direct binding ELISA to human IL-5, and a concentration that was about 3 times the apparent 50% point was used in competition assays. This concentration corresponded to about 30 ng of biotinylated antibody JES1-39D10.

Competition assays were carried out in which binding of the biotinylated antibody to plates coated with human IL-5 was measured in the presence of unlabelled antibody JES1-39D10 or antibody CMX5-1, CMX5-2 or CMX5-5, each of which had been purified by protein A/G affinity chromatography.

EIA plates were treated with 0.1 M $NaHCO_3$, pH 9.2, for 1 hour at room temperature. Human IL-5 in TBS was then added at 100 μg per well. The plates were incubated overnight at 4° C. and then blocked with 3% BSA-TBS ml for 1 hour at room temperature. Fifty microliters of 2-fold serially diluted competing antibodies plus the appropriate amount of biotinylated antibody JES1-39D10 (also in a 50 II volume) were added to each well, and the plates were incubated for 1 hour at room temperature.

The plates were then washed 5 times with TBS-Tween-20, incubated with 1 μg/ml horseradish peroxidase (HRP)-streptavidin conjugate for 1 hour at room temperature, washed 5 times with TBS-Tween-20, and developed with HRP substrate TMB. Absorbance of the samples was then measured spectrophotometrically at 450 nm.

The results showed that whereas unlabeled antibody JES1-39D10 competed with its biotinylated form at an approximately 1:1 ratio, the same degree of competition by antibodies CMX5-1, 2 and 5 required greater amounts of the antibodies. Taking the molar ratio of unlabeled to biotinylated antibody JES1-39D10 to be 1.0, the molar ratios of antibodies CMX5-1, 2 and 5 to biotinylated JES1-39D10 needed to produce the same degree of binding inhibition were estimated to be 3.3, 1.4 and 1.4, respectively.

Inhibition of Human IL-5 Receptor Binding

In an investigation of the ability of humanized antibodies CMX5-1, 2 and 5 to inhibit the binding of radiolabeled human IL-5 to recombinant human IL-5 receptor a chains on transfected COS cells, it was found that all three antibodies blocked receptor binding. This blocking activity was observed using both conditioned media and the purified antibodies. With a constant 0.5 nM concentration of the labeled IL-5, the concentrations of antibodies CMX5-1, 2 and 5 required to cause 50% inhibition of receptor binding ($IC_{50}$) were calculated to be 1.5–3.0, 0.35–0.7 and 0.5–1.1 nM, respectively. The $IC_{50}$ for wild-type antibody JES1-39D10 was determined to be 0.15–0.55 nM.

Modification of Antibody CMX5-5 Light Chain

All five of the humanized antibodies contained an aspartic acid residue at position 105 of the light chain due to DNA modifications made to facilitate cloning. To restore the native sequence, the aspartic acid residue at position 105 was replaced with a glutamic acid residue in the light chain of antibody CMX5-5. This was done by using a synthetic oligonucleotide designated B3289CC (SEQ ID NO: 66) having an amino acid sequence corresponding to that of the junction of carboxyl-terminal peptide of VL and the amino-terminal peptide of the CL, with a GAC to GAG codon change. This codon change created a XhoI restriction site in place of an SalI site.

PCR was performed with oligonucleotide primers B3289CC and A2496CC (SEQ ID NO: 34), using the CMX5-5 light chain as the template. The resulting DNA fragment was gel-purified, restricted, and used to replace the SalI/EcoRI fragment in the pSRS-based CMX5-5 light chain cDNA. The modified CMX5-5 light chain cDNA was then excised from pSRS and cloned into pDSRG for stable expression. A new variant, consisting of the CMX5-2 heavy chain and the modified CMX5-5 light chain, was designated CMX5-OK1. Another variant, consisting of the CMX5-5 heavy chain and the modified CMX5-5 light chain, was designated CMX5-OK2.

Biological Effects

Inhibition of IL-5-induced CD11b Expression

An HL-60 (ATCC CCL 240) subclone was maintained in Iscoves' Modified Dulbecco's Medium (JRH BioSciences) supplemented with 10% FBS, 2mM glutamine, and penicillin-streptomycin. HL-60 is a multipotent human pro-myelocytic cell line which, in the presence of butyrate or human IL-5, yields cells that develop the phenotypic characteristics of eosinophils [Tomonaga et al., *Blood* 67:1433 (1986); Fabian et al., *Blood* 80:788 (1992)]. Increased expression of a cell adhesion molecule called CD11b/CD18 has been observed on the surface of eosinophils that were activated and recruited to the lung of allergic patients [Georas et al., *Am. J. Resp. Cell Mol. Biol.* 7:261 (1992)].

Prior to assay, the HL-60 cells were primed for differentiation by growth in alkaline medium (pH adjusted to 7.6–7.8 with NaOH or sodium bicarbonate) for one week. Following the period of growth, the cells were transferred to 24-well culture dishes at a density of $2 \times 10^5$ cells/ml. Serially diluted test antibodies was preincubated with a constant amount of human IL-5 at 37° C. for one hour and then added to the cells. The final concentration of IL-5 in the culture was 150 pM.

Seventy-two hours later, the cells were harvested by centrifugation and resuspended at a concentration of $1 \times 10^6$ cells/ml and 50 μl volumes ($5 \times 10^4$ cells) were aliquoted per well in a 96-well microtiter plate. The cells were dried in the wells and then washed with 70% ethanol followed by TBS-Tween-20, and blocked with 10% non-fat dried milk and 5% BSA.

The primary antibody (mouse anti-human CD11b; Becton-Dickinson, Braintree, Mass.) was added. After a two-hour incubation at 37° C., the plates were treated sequentially by washing 3X with TBS-tween-20, allowing a secondary antibody against the primary antibody (Jackson ImmunoResearch Laboratories, West Grove, Pa.) to bind, and washing again 3X with TBS-Tween-20. Specifically bound antibody was then detected using an ELISA Amplification System (Gibco-BRL).

It was found that humanized antibodies CMX5-1, CMX5-2 and CMX5-5 were all able to block the CD11b induction activity of human IL-5. The relative $IC_{50}$, were estimated to be as follows:

| SAMPLE | $IC_{50}$ (pM) | MOLAR RATIO CMX5/IL-5 | $IC_{50}$ CMX5/$IC_{50}$ 39D10 |
|---|---|---|---|
| CMX5-1 | 1467 | 7.3:1 | 8.8 |
| CMX5-2 | 467 | 2.3:1 | 2.8 |
| CMX5-5 | 800 | 4:1 | 4.8 |
| 39D10 | 166 | 0.83:1 | 1 |

As can be seen from the Table, humanized antibodies CMX5-2 and CMX5-5 appeared to be more potent than antibody CMX5-1.

Inhibition of Allergen-induced Mouse Eosinophilia

To determine whether the humanized antibodies were capable of neutralizing the activity of IL-5 in vivo, young male B6D2F1/J mice were sensitized with alum-precipitated ovalbumin, using 8 mg per animal. One week thereafter a booster dose was given. Except for a group of 5 unsensitized control mice, all other groups contained 6 mice.

One week after the booster and prior to challenge, the sensitized animals were injected intraperitoneally with test antibodies in a volume of 0.5 ml. Each group received one of the following: 0.1 mg of antibody JES1-39D10 per kilogram of body weight, 1 mg of antibody JES1-39D10 per kilogram of body weight, 1 mg of antibody CMX5-1 per kilogram of body weight, and 10 mg of antibody CMX5-1 per kilogram of body weight. An antibody designated TRFK 5, a rat anti-mouse IL-5 monoclonal antibody (Schumacher et al., supra), was used as a positive control. The control sensitized mice received saline.

The animals were then challenged twice with ovalbumin aerosol for 1 hour. Twenty-four hours following the challenge, bronchioalveolar lavage, peripheral blood, and lung-tissue specimens were collected, fixed, developed by eosinophil-specific staining dyes, and examined microscopically to determine eosinophil distribution.

Mice that received antibody CMX5-1 at the 10 mg per kilogram body of weight dose were found to have significantly reduced numbers of eosinophils in their bronchioalveolar lavage fluid, whereas less quantitative changes were observed with other cell types. Mice that received antibody JES1-39D10 also had reduced eosinophil levels.

Hybridoma Deposit

The hybridoma cell line (JES1-39D10.11) producing monoclonal antibody JES1-39D10 was deposited Jan. 8, 1992 with the American Type Culture Collection (ATCC), Rockville, Md., and assigned Accession No. ATCC HB 10959. These deposits were made under conditions as provided under ATCC's agreement for Culture Deposit for Patent Purposes, which assures that the deposits will be made available to the US Commissioner of Patents and Trademarks pursuant to 35 USC 122 and 37 CFR 1.14 and will be made available to the public upon issue of a U.S. patent, and which requires that the deposits be maintained. Availability of the deposited strains is not to be construed as a license to practise the invention in contravention of the rights granted under the authority of any government in accordance with its patent laws.

Many modifications and variations of this invention can be made without departing from its spirit and scope, as will become apparent to those skilled in the art. The specific embodiments described herein are offered by way of example only, and the invention is to be limited only by the terms of the appended claims.

What is claimed is:

1. A monoclonal antibody or fragment thereof which specifically binds to human interleukin-5 comprising a heavy chain variable region defined by SEQ ID NO: 1 and/or a light chain variable region defined by SEQ ID NO: 2.

2. A hybridoma secreting a monoclonal antibody which specifically binds human interleukin-5, said antibody having a heavy chain variable region defined by SEQ ID NO: 1 and/or a light chain variable region defined by SEQ ID NO: 2.

3. A binding composition capable of specifically binding to human interleukin-5 comprising a polypeptide comprising an amino acid sequence defined by SEQ ID NO: 1 or SEQ ID NO:2.

4. The binding composition of claim 3 wherein the amino acid sequence is defined by SEQ ID NO: 1.

5. The binding composition of claim 3 wherein the amino acid sequence is defined by SEQ ID NO: 2.

6. An isolated DNA which comprises a nucleotide sequence encoding a polypeptide comprising an amino acid sequence defined by SEQ ID NO: 1 or 2.

7. The DNA of claim 6 which encodes a polypeptide comprising the amino acid sequence defined by SEQ ID NO: 1.

8. The DNA of claim 7 comprising the nucleotide sequence defined by SEQ ID NO: 1.

9. The DNA of claim 6 which encodes a polypeptide comprising the amino acid sequence defined by SEQ ID NO: 2.

10. The DNA of claim 9 comprising the nucleotide sequence defined by SEQ ID NO: 2.

11. A recombinant vector comprising the DNA of claim 6.

12. A host cell comprising the recombinant vector of claim 11.

13. A method of making a polypeptide comprising culturing the host cell of claim 12 under conditions in which the DNA is expressed.

14. A humanized monoclonal antibody or fragment thereof which specifically binds to human interleukin-5 and comprises complementarity determining regions from the heavy and light chain variable regions of the monoclonal antibody of claim 1.

15. The humanized monoclonal antibody of claim 14 comprising a heavy or light chain variable region comprising a mature amino acid sequence set forth in SEQ ID NO: 36, 37, 40, 41, 46, 47, 56, 57, 64 or 65.

16. The humanized monoclonal antibody of claim 14 comprising a heavy chain variable region comprising the mature amino acid sequence defined in SEQ ID NO: 36 and a light chain variable region comprising the mature amino acid sequence set forth in SEQ ID NO: 37.

17. The humanized monoclonal antibody of claim 14 comprising a heavy chain variable region comprising the mature amino acid sequence defined in SEQ ID NO: 40 and a light chain variable region comprising the mature amino acid sequence set forth in SEQ ID NO: 41.

18. The humanized monoclonal antibody of claim 14 comprising a heavy chain variable region comprising the mature amino acid sequence defined in SEQ ID NO: 46 and a light chain variable region comprising the mature amino acid sequence set forth in SEQ ID NO: 47.

19. The humanized monoclonal antibody of claim 14 comprising a heavy chain variable region comprising the mature amino acid sequence defined in SEQ ID NO: 56 and a light chain variable region comprising the mature amino acid sequence set forth in SEQ ID NO: 57.

20. The humanized monoclonal antibody of claim 14 comprising a heavy chain variable region comprising the mature amino acid sequence defined in SEQ ID NO: 64 and a light chain variable region comprising the mature amino acid sequence set forth in SEQ ID NO: 65.

21. A binding composition capable of specifically binding to human interleukin-5 comprising a polypeptide comprising a variable region of a humanized monoclonal antibody which comprises a mature amino acid sequence defined by SEQ ID NO: 36, 37, 40, 41, 46, 47, 56, 57, 64 or 65.

22. An isolated DNA which comprises a nucleotide sequence encoding a mature amino acid sequence defined by SEQ ID NO: 36, 37, 40, 41, 46, 47, 56, 57, 64 or 65.

23. A recombinant vector comprising the DNA of claim 22.

24. A host cell comprising the recombinant vector of claim 23.

25. A method of making a polypeptide comprising culturing the host cell of claim 24 under conditions in which the DNA is expressed.

26. A pharmaceutical composition comprising the humanized monoclonal antibody of claim 14 and a pharmaceutically acceptable carrier.

27. An IL-5 binding protein comprising complementary determining regions from the heavy and/or light chain variable regions of the monoclonal antibody of claim 1.

28. The IL-5 binding protein of claim 27 which is a single chain IL-5 binding protein.

29. The binding composition of claim 3, wherein the polypeptide which comprises an amino acid sequence defined by SEQ ID NO: 1 and SEQ ID NO: 2.

30. The DNA of claim 6 which encodes an amino acid sequence defined by SEQ ID NO: 1 and SEQ ID NO: 2.

* * * * *